(12) United States Patent
Agar

(10) Patent No.: US 12,171,854 B2
(45) Date of Patent: Dec. 24, 2024

(54) HETEROCYCLIC-DITHIOL CLICK CHEMISTRY

(71) Applicant: Northeastern University, Boston, MA (US)

(72) Inventor: Jeffrey N. Agar, Falmouth, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 17/695,166

(22) Filed: Mar. 15, 2022

(65) Prior Publication Data

US 2022/0273540 A1 Sep. 1, 2022

Related U.S. Application Data

(63) Continuation of application No. 16/630,330, filed as application No. PCT/US2018/041581 on Jul. 11, 2018, now abandoned.

(60) Provisional application No. 62/680,318, filed on Jun. 4, 2018, provisional application No. 62/530,934, filed on Jul. 11, 2017.

(51) Int. Cl.
| | | |
|---|---|---|
| *A01N 43/50* | (2006.01) | |
| *A01N 43/56* | (2006.01) | |
| *A61K 8/49* | (2006.01) | |
| *A61K 8/58* | (2006.01) | |
| *A61K 8/65* | (2006.01) | |
| *A61K 47/22* | (2006.01) | |
| *A61Q 3/02* | (2006.01) | |
| *A61Q 5/00* | (2006.01) | |
| *C07D 401/04* | (2006.01) | |
| *C08F 283/06* | (2006.01) | |
| *C08F 289/00* | (2006.01) | |
| *C08G 75/06* | (2006.01) | |
| *C09D 1/00* | (2006.01) | |
| *C09D 171/02* | (2006.01) | |
| *C09D 181/02* | (2006.01) | |
| *C09D 189/00* | (2006.01) | |
| *C12N 11/08* | (2020.01) | |
| *C25D 11/00* | (2006.01) | |

(52) U.S. Cl.
CPC .............. *A61K 8/4986* (2013.01); *A61K 8/58* (2013.01); *A61K 8/65* (2013.01); *A61K 47/22* (2013.01); *A61Q 3/02* (2013.01); *A61Q 5/00* (2013.01); *C08F 283/06* (2013.01); *C08F 289/00* (2013.01); *C08G 75/06* (2013.01); *C09D 1/00* (2013.01); *C09D 171/02* (2013.01); *C09D 181/02* (2013.01); *C09D 189/00* (2013.01); *C12N 11/08* (2013.01); *C25D 11/00* (2013.01); *C08G 2150/00* (2013.01)

(58) Field of Classification Search
CPC ........ A61K 8/8147; A61K 8/04; A61K 8/342; A61K 8/416; A61K 8/4973; A61K 8/817; A61K 8/898; A61K 2800/10; A61K 2800/5424; A61K 2800/594; A61K 2800/596; A61K 8/922; A61Q 5/12
See application file for complete search history.

(56) References Cited

U.S. PATENT DOCUMENTS

| | | |
|---|---|---|
| 9,556,308 B1 | 1/2017 | Waymouth et al. |
| 9,962,691 B2 | 5/2018 | Ragheb et al. |
| 10,357,766 B2 | 7/2019 | Ragheb et al. |
| 2007/0270548 A1 | 11/2007 | Bojkova et al. |
| 2010/0209375 A1 | 8/2010 | Deboni et al. |
| 2013/0211055 A1 | 8/2013 | Raines et al. |
| 2015/0284478 A1 | 10/2015 | Agar et al. |
| 2015/0376591 A1 | 12/2015 | Raines et al. |
| 2021/0161789 A1 | 6/2021 | Agar |

FOREIGN PATENT DOCUMENTS

| | | |
|---|---|---|
| JP | 2010150255 A | 7/2010 |
| WO | WO-2007/049658 A1 | 5/2007 |
| WO | WO-2014/078623 A2 | 5/2014 |
| WO | WO-2019/014311 A1 | 1/2019 |

OTHER PUBLICATIONS

Elbert et al. Journal of Controlled Release 76 (2001) 11-25. (Year: 2001).*
Aluri et al., "Cyclic Thiosulfinates as a Novel Class of Disulfide Cleavable Cross-Linkers for Rapid Hydrogel Synthesis," Bioconjugate Chemistry, 32: 584-594 (2021).
Barcan et al., "Structurally Dynamic Hydrogels Derived from 1,2-Dithiolanes," Journal of the American Chemical Society, 137:5650-5653 (2015).
Extended European Search Report for EP Application No. 18831974.3 dated Nov. 6, 2020.
International Search Report and Written Opinion for International Application No. PCT/US18/41581 mailed Dec. 6, 2018.
Karch et al., "A Limited Role for Disulfide Cross-linking in the Aggregation of Mutant SOD1 Linked to Familial Amyotrophic Lateral Sclerosis," The Journal of Biological Chemistry, 283:13528-13537 (2008).
Pubmed Compound Summary for CID 79045, "1,2-Dithiolane," U.S. National Library of Medicine, (2005).
Salisbury et al., "Cyclic disulfide-mediated stabilization of neurodegenerative disease-associated proteins SOD1 and DJ-1," Brandeis Univ, (209 pages) (2013).

* cited by examiner

*Primary Examiner* — Mina Haghighatian
*Assistant Examiner* — Janice Y Silverman
(74) *Attorney, Agent, or Firm* — Foley Hoag LLP; Dana M. Gordon; Lawrence P. Tardibono

(57) ABSTRACT

Disclosed are polymers, methods of making polymers, and compositions, focused on cross-linking heterocycles comprising a moiety of Formula I with thiols and thiolates.

15 Claims, 18 Drawing Sheets

HETEROCYCLIC-DITHIOL CLICK CHEMISTRY

RELATED APPLICATIONS

This application is a continuation of U.S. patent application Ser. No. 16/630,330, filed Jan. 10, 2020; which is a U.S. National Stage Application of International Application No. PCT/US18/41581, filed Jul. 11, 2018; which claims the benefit of priority to U.S. Provisional Application No. 62/530,934, filed Jul. 11, 2017; and U.S. Provisional Application No. 62/680,318, filed Jun. 4, 2018.

FIELD

The present disclosure relates to methods for forming covalent bonds between molecules or molecular species of interest.

BACKGROUND

The covalent coupling of two molecules or molecular species is a fundamentally important chemical reaction that is widely used in areas as diverse as production and tagging of biomolecules, polymer synthesis, synthesis of complex molecular architectures, such as dendrimers, and surface chemistry. "Click" chemistry has played an important part in recent developments in this field. The concept of click chemistry was first introduced in 2001.[1]

The term "click" reaction is generally used to describe a chemical reaction that occurs in one pot, is not sensitive to water, generates minimal and inoffensive by-products, and has a high thermodynamic driving force that drives it quickly and irreversibly to a high yield of a single reaction product, with high reaction specificity. Typical click reactions include cycloadditions of unsaturated species, such as addition of azides to alkynes; nucleophilic substitutions; carbonyl chemistry of the "non-aldol" type; and additions of carbon-carbon multiple bonds, including Diels-Alder chemistry.

Click reactions are particularly suitable for carrying out reactions in complex biological environments in which the reactions need to be regiospecific, high yielding, any by-products need to be non-toxic (for in vivo systems) and the products of the reaction need to be physiologically stable.

The thiolate group has unique nucleophilicity and polarizatbility, enabling it to be targeted with high specificity. The thiolate-ene reaction has a large thermodynamic driving force, has high reaction yields, is stereospecific, and is accepted as a type of click chemistry.[2] Numerous drugs form covalent bonds to cysteine (Cys) thiolates. Using submicromolar-affinity kinase inhibitors to minimize off-target reactions, -ene, -yne, and other weakly electrophilic warheads have been used to increase specificity for kinases with a particular (Cys-containing) structure.[3]

Thiol-ene reactions are also prevalent in applications requiring thiol cross-linking.[4] Synthetic applications of thiol-ene cross-linking reactions include: self-healing polymers,[2] nanogels,[3] thermosetting polymers, hydrogels,[5] and dendrimers.[6] Prevalent biochemical applications of thiol-ene cross-linking include functionalizing or stabilizing biotherapeutics in vitro,[7] and probing high-order protein structure and protein-protein interactions.[8]

Dithiolate-diene reactions can also template higher order structures in materials ranging from plastics to proteins. Unfortunately, -ene moieties are not bioorthogonal and indiscriminately bind many of the hundreds of cysteines residues in the biological milieu essential for protein function, for example the lone catalytic cysteine residue in phosphatases and cysteine proteases. This results in levels of toxicity that limit the in vivo applications of thiol-ene chemistry.

One shortcoming of these thiol-ene cross-linking tools is that they are not cross-linking selective. These tools will form terminal "dead-end" modifications unless two functional groups happen to be within their reach.[9] Dead-end modifications are toxic in vivo; in particular the modification of essential catalytic cysteines (e.g., phosphatases and cysteine [Cys] proteases) and the creation of "non-self" epitopes that increase the risk of an adverse immune response.[9] This inherent toxicity and poor cell permeability have stymied the use of in vivo cross-linking.

Thus, there is a need for a biocompatible replacement for dienes in dithiolate-diene reactions. Alternatively, or in addition, there is a need for a chemical tool with improved selectivity for cross-linking thiols. Alternatively, or in addition, there is a need for new simple, clean, and highly efficient immobilization chemistries, which are applicable to a broad class of biomolecules.

SUMMARY

In a first aspect, the present disclosure provides a method for covalent coupling of molecules, the method comprising
providing a plurality of first molecules comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring, and
contacting the plurality of first molecules with a plurality of second molecules comprising at least one thiol functional group,
thereby forming a plurality of covalent bonds between the S or Se atoms of the first molecules and the free thiol groups of the second molecules.

In a second aspect, the present disclosure provides a polymer derived from a first monomer and a first cross-linker, wherein
the first monomer comprises at least two thiol functional groups;
the first cross-linker comprises a moiety of Formula I:

Formula I wherein
W is independently selected from the group consisting of S and Se;
Y is independently selected from the group consisting of S, Se, S(O), Se(O), S(O)$_2$ and Se(O)$_2$; and X together with W and Y forms a substituted or unsubstituted 3-10-membered heterocyclic ring.

In a third aspect, the present disclosure provides a method for producing a dendrimer, the method comprising:
(i) providing a plurality of first core dendrimer precursor molecules comprising at least three thiol functional groups; and
contacting the plurality of first core dendrimer precursor molecules with a plurality of first cross-linkers comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; or
(ii) providing a plurality of second core dendrimer precursor molecules comprising at least three moieties of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; and
contacting the plurality of second core dendrimer precursor molecules with a plurality of second cross-linkers comprising at least two thiol functional groups,
under conditions to enable a reaction to occur between the thiol functional groups and the moieties of Formula I, thereby forming the dendrimer by covalently cross-linking the core precursor dendrimer molecules with the cross-linkers.

In some embodiments, the methods of the first and third aspects, and the polymers of the second aspect, involve click chemistry reactions because they proceed in high yield, with stereoselectivity, at a high reaction rate, and are driven by a thermodynamic driving force.

Advantageously, the moieties of Formula I are more biocompatible than dienes (or other commonly used electrophiles) that have been used to cross-link thiols.

In some embodiments of the first to third aspects,
X is —(CR$^1$R$^2$)$_n$—, wherein n is an integer selected from the group consisting of 1, 2, 3, 4, 5, 6, 7 and 8; and
each R$^1$ and each R$^2$ on each CR$^1$R$^2$ group is independently selected from the group consisting of: H, OH, NO$_2$, CN, NH$_2$, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_2$-C$_{12}$heteroalkyloxy, optionally substituted C$_3$-C$_{12}$cycloalkyloxy, optionally substituted C$_3$-C$_{12}$cycloalkenyloxy, optionally substituted C$_1$-C$_{12}$heterocycloalkyloxy, optionally substituted C$_2$-C$_{12}$heterocycloalkenyloxy, optionally substituted C$_6$-C$_{18}$aryloxy, optionally substituted C$_1$-C$_{18}$heteroaryloxy, optionally substituted C$_1$-C$_{12}$alkylamino, CONR$^3$R$^4$, NR$^3$COR$^4$, NR$^3$COOR$^4$, NR$^3$SO$_2$R$^4$, NR$^3$CONR$^3$R$^4$, and NR$^3$R$^4$, and
wherein each R$^3$ and R$^4$ is independently selected from the group consisting of: H, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, and optionally substituted C$_1$-C$_{18}$heteroaryl.

In some embodiments of the third aspect, the plurality of first core dendrimer precursor molecules comprising at least three thiol functional groups can be formed by a thiol-ene reaction between a dithiol, such as 1,3 propane dithiol or 1,4 butane dithiol, with a trialkene, such as 2,4,6-tris(allyloxy)-1,3,5-triazine. In some embodiments, this method can be used to create "self-healing" dendritic superstructures whose properties can be controlled by the ratio of core dendrimer precursor molecules and extender molecules. Alternatively, trithiol compounds and tetrathiol compounds can be cross-linked to provide the core dendrimer precursor molecule having at least three thiol functional groups. The cross-linker may comprise moieties of Formula I.

In a fourth aspect, the present disclosure provides a method for producing a polymer or dendrimer, the method comprising:
providing a plurality of first monomers comprising at least two thiol functional groups;
contacting the plurality of first monomers with a plurality of first cross-linkers comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring,
under conditions to enable a reaction to occur between the thiol functional groups and the cross-linker, thereby forming the polymer or the dendrimer by covalently cross-linking the monomers via the cross-linker molecule.

In a fifth aspect, the present disclosure provides a method of coating a surface of an object, a device, or an assembly, comprising the steps of:
(a) providing a surface of an object, a device, or an assembly;
(b) contacting the surface with a plurality of first molecules comprising a reactive moiety and a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; and
thereby forming a plurality of covalent bonds between the surface and the reactive moieties of the first molecule to form a first monolayer.

In an example of the fifth aspect, beta-lipoic acid can be bound to the surface using the carboxylic moiety. This will form an electrochemically active monolayer (i.e., a first monolayer) that (before electrons are applied) can perform a click reaction with functionalized dithiols, forming a bilayer (i.e., a first bilayer). In some embodiments, the first bilayer is a semiconductor. After electrons are applied the disulfide bonds can be reduced to create a monolayer (i.e., a second monolayer). In some embodiments, the second monolayer will chelate metals forming a bilayer (i.e., a second bilayer). In some embodiments, the second bilayer is a semiconductor with a P—N gap that is tunable by the identity of the metal chelated. To the metal layer a third layer of heterocyclics comprising a moiety of Formula I (e.g., cyclic disulfides or cyclic thiosulfinates) for a trilayer. In some embodiments, the formation of the trilayer depends upon the redox state of the metals, which can be controlled by an applied voltage. In some embodiments, the trilayer system is a battery. In some embodiments, the cyclic thiosulfinate acts analogously to the S8 used in second generation lithium ion batteries.

The methods of the first, third and fourth aspects provide reactions that and the second aspect provides polymers that can be used to create self-healing polymers, hydrogels, nanogels, thin films, metal nanoparticles, and two layers within a material. In some embodiments, the methods and polymers can be used for functionalizing, preventing corrosion of, pacifying, and passivating surfaces. In some embodiments, the methods and polymers can be used for synthetic click chemistry. In some embodiments, the methods and polymers can be used to make photochromic agents and flavorants. In some embodiments, the methods and polymers can be used for functionalization of ionic liquids. In some embodiments, the methods and polymers can be used for creating self-assembled monolayers and molecular scale electronics. In some embodiments, the methods and polymers can be used for superconductors. In some embodiments, the methods and polymers can be used for batteries.

Important features of the reactions occurring in the first, third and fourth aspects, and of polymers of the second aspect, include that: 1) binding to single thiolates is reversible but dithiol cross-linking is not; 2) the leaving group is only expended upon cross-linking; 3) once a disulfide bond is formed to first thiol moiety, the EC of the second thiol moiety increases exponentially (i.e., release from the first thiol via ring closure and forming a cross-link have similar entropy); 4) cross-linking is driven by the considerable bond enthalpies of S—S, S—Se or Se—Se bond and water formation; high yields; and well-established stereoselectivity; 5) other reactive functional groups, including carboxylates, amines, and disulfides, are avoided.

Reversible cyclic disulfide binding to the transferrin receptor Cys has previously been utilized for transport across cell membranes, such as for drug cargo delivery. On this basis, the compounds of Formula I may be used for similar applications. Thus, in a sixth aspect, provided herein is a method for transporting a molecule of interest across a cell membrane comprising:
(a) providing a functionalized molecule of interest comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a 3-10-membered cyclic ring; and
(b) contacting a cell of interest with the functionalized molecule of interest under conditions for the moiety of Formula I to reversibly bind to one or more cell membrane transport proteins,
thereby facilitating transport of the molecule of interest across the cell membrane.

BRIEF DESCRIPTION OF THE FIGURES

Embodiments of the present invention will be discussed with reference to the accompanying figures wherein.

DETAILED DESCRIPTION

Figure 1A:
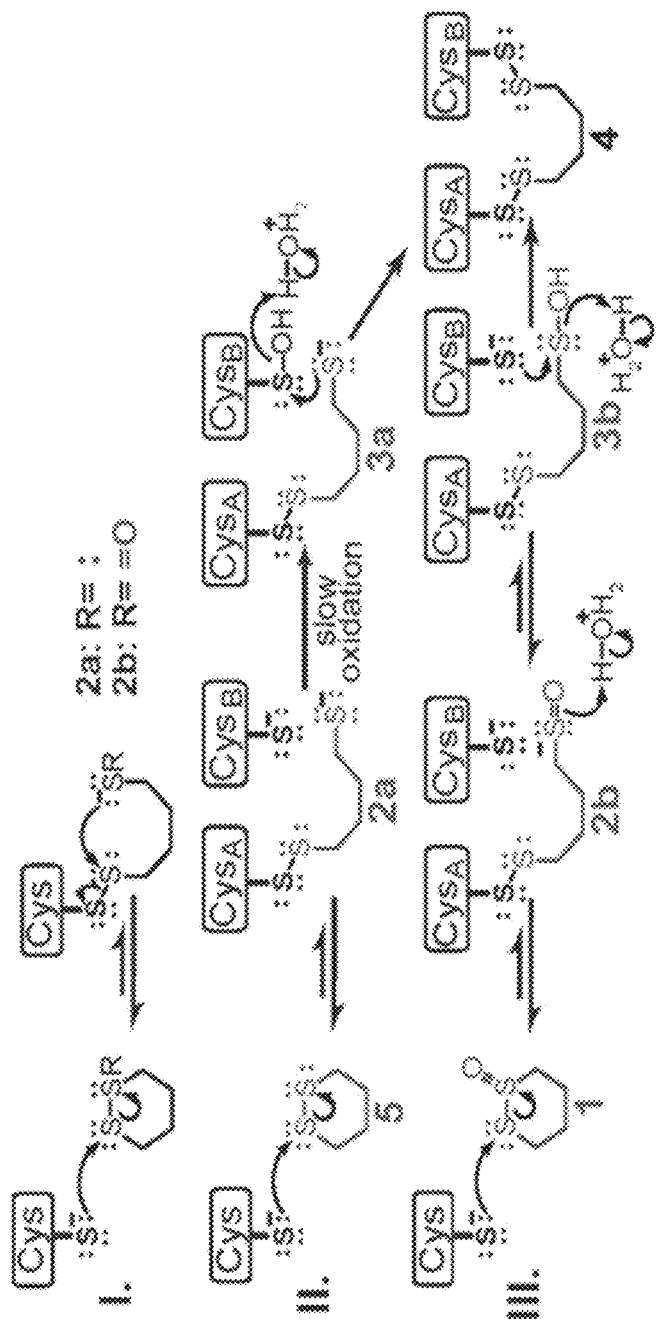
FIG. 1A. Without being bound by any theory, proposed mechanism of thiol cross-linking using cyclic disulfides and cyclic thiosulfinates. Formation of the first disulfide bond is reversible. Dead-end modification is minimized by entropically favorable ring closure (Mechanism I). Cross-linking proceeds through condensation of Cys$_A$, and a sulfenic acid derived from either rate limiting S-oxidation of thiolate$_B$ (Mechanism II) or a cyclic thiosulfinate (Mechanism III).

Disclosed herein are polymers, methods of making polymers, and compositions, focused on a more biocompatible method for cross-linking thiols and thiolates. In some embodiments of the present disclosure, polymers, methods of making, and compositions focus on the reaction of dithiols and dithiolates with heterocycles. In some embodiments of the present disclosure, polymers, methods of making, and compositions focus on the reaction of thiols and thiolates with heterocycles. In some embodiments, the heterocycles comprise a moiety of Formula I:

Formula I wherein
W is independently selected from the group consisting of S and Se;
Y is independently selected from the group consisting of S, Se, S(O), Se(O), $S(O)_2$ and $Se(O)_2$; and
X together with W and Y forms a substituted or unsubstituted 3-10-membered heterocyclic ring. In cyclic disulfides, W and Y are S. In some embodiments, the heterocycle is a cyclic thiosulfinate, wherein W is S and Y is S(O). In some embodiments, the heterocycle is a cyclic diselenide, wherein W and Y are Se. In some embodiments, the heterocycle is a cyclic selenoselenoxide, wherein W is Se and Y is Se(O). In some embodiments, the heterocycle is a cyclic selenosulfide, wherein W is Se and Y is S; or W is S and Y is Se. In some embodiments, the heterocycle is a cyclic selenosulfinate, wherein W is Se and Y is S(O). In some embodiments, the heterocycle is a cyclic thioselenoxide, wherein W is S and Y is Se(O).

Thiols, thiolates, dithiols, and dithiolates are used in a variety of chemical reactions. In some embodiments, the heterocycle comprising a moiety of Formula I is used to replace an electrophile (e.g., an -ene molecule, an -yne molecule, a Michael acceptor, etc.) in thiol-electrophile mediated cross-linking. In some embodiments, the heterocycle comprising a moiety of Formula I reacts with a thiol, a thiolate, a dithiol, or a dithiolate in the cross-linking of self-healing polymers,[8] hydrogels,[9] nanogels,[10] thin films,[11] metal nanoparticles,[12] and two layers within a material.[13] In some embodiments, the reactions and methods disclosed herein are used in functionalizing,[14] preventing corrosion of,[15] pacifying,[16] and passivating surfaces. In some embodiments, the reactions and methods disclosed herein are used for synthetic click chemistry (e.g., use a dithiol such as benzene dithiol to react with oxo-cyclic disulfides). In some embodiments, the reactions and methods disclosed herein catalyze click chemistry (serving as Cu ligand).[17] In some embodiments, the reactions and methods disclosed herein are used to make photochromic agents' and flavorants. In some embodiments, the reactions and methods disclosed herein are used for the functionalization of ionic liquids.[19] In some embodiments, the reactions and methods disclosed herein are used to create self-assembled monolayers and molecular scale electronics.[20] In some embodiments, the reactions and methods disclosed herein are used for superconductors.[21] In some embodiments, the reactions and methods disclosed herein are used for capacity retention in lithium-sulfur batteries.[22] The most prevalent mechanisms employed for in vitro polymerization and surface chemistry are thiol-ene click chemistry (both radical- and Michael-types) and metal ligation, respectively.

In some embodiments, the reactions and methods disclosed herein are analogous to using dienes, wherein the diene is replaced by a more biocompatible heterocycle comprising a moiety of Formula I (e.g., a cyclic disulfide). The methods described herein differ from that of Barcan[23] whenever a cyclic disulfide is used as the group of Formula I, and when the cyclic disulfide is not used as the cross-linker, it differs from Barcan's methods by employing one dithiol per cylic disulfide, which therefore does not result in the formation of any free thiol that need to be capped/functionalized (in Barcan's case using maleimide thiol-ene chemistry).

The reactions and methods described herein address the need for chemical tools that can selectively form cross-links. Contemporary thiol-selective cross-linkers, for example, modify all accessible thiols, but only form cross-links between a subset. The resulting terminal "dead-end" modifications of lone thiols are toxic, confound cross-linking-based studies of macromolecular structure, and are an undesired—and currently unavoidable—by-product in polymer synthesis.

As exemplified by thiolate-ene "click" chemistry, the unique properties of thiolates enable highly selective reactions. Dithiol-diene reaction partners can template high order structures and are employed (in vitro) in polymer syntheses, in biochemical probes, and to stabilize proteins. Unfortunately, enes react with a myriad of essential protein cysteine residues, resulting in toxicity that limits their applicability in vivo. A more biocompatible and/or selective method for cross-linking thiolate pairs was sought. It was reasoned that cyclic thiosulfinates—S-oxo derivatives of well-tolerated cyclic disulfide natural products—would selectively cross-link dithiols. Without being bound by any theory, the following mechanism is proposed: a nucleophilic attack by thiolate A (e.g., $Cys_A$) upon the thiosulfinate disulfide results in thiolate-disulfide interchange concomitant to ring cleavage, and a disulfide tethered terminal sulfenic acid moiety (FIG. 1A). Next, a nucleophilic attack by thiolate B on the sulfenic sulfur results in the formation of a second disulfide bond coupled to the release of water and a cross-link (FIG. 1A). It was also reasoned that a similar mechanism would occur with cyclic selenoselenoxides, cyclic thioselenoxides and cyclic selenosulfinates.

In some embodiments, important attributes of dithiol-cyclic thiosulfinate chemistry include: 1) avoiding binding to lone cysteines (for example the proteins in a human that one does not want a cross-linker to react with) is reversible, whereas cross-linking of dithiols is not; 2) the cross-linking step is driven by the considerable bond enthalpies of disulfide bond and water formation; 3) most of the attributes of click chemistry including orthogonality with other protein functional groups, high reaction yields, rapid reactions, stereoselectivity, compatibility with aqueous solvents, and a ring strain-dependence that is orders of magnitude higher than existing period 2 element systems.

Figure 1B:
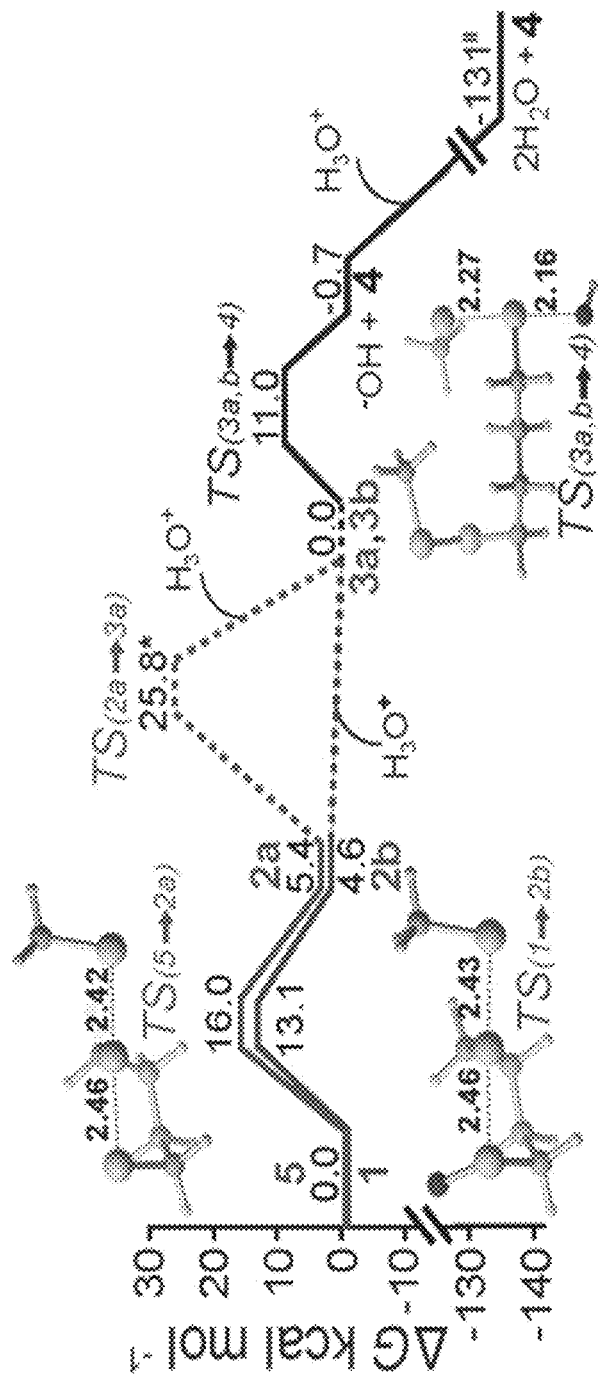
FIG. 1B. A potential energy surface for the non-enzymatic reaction according to the mechanism proposed in FIG. 1A. The free energy values are computed using M06-2X/6-311+G(d,p) IEF-PCM$^{H2O}$/m06-2X/6-31+G(d,p) IEF-PCM$^{H2O}$. *The dotted upper line indicates an activation barrier derived from the zeroth-order half-life kinetics of the oxidation of 5. $^{\eta}\Delta G$=−132.4 kcal mol$^{-1}$ computed through DFT: $\Delta G$=−131 kcal mol$^{-1}$ from published enthalpies of S—S bond and water formation. Transition structures for the nucleophilic addition of MeS$^{-}$ to 1 and 5 are shown. The bond lengths and energy values are reported in Å and kcal mol$^{-1}$, respectively.

Using the thiol pair of Cu/Zn-superoxide dismutase (SOD1) it was demonstrated that cyclic disulfides—including the drug/nutritional supplement lipoic acid—efficiently cross-linked thiol pairs but avoided dead-end modifications. Thiolate-directed nucleophilic attack upon the cyclic disulfide resulted in thiol-disulfide exchange and ring cleavage. The resulting disulfide-tethered terminal thiolate moiety either directed the reverse reaction, releasing the cyclic disulfide, or participated in oxidative disulfide (cross-link) formation (FIG. 1A). It was hypothesized—and confirmed with density functional theory (DFT) calculations—that mono-S-oxo derivatives of cyclic disulfides formed a terminal sulfenic acid upon ring cleavage that obviated the previously rate-limiting step, thiol oxidation, and accelerated the new rate-determining step, ring cleavage. Without being bound by any theory, the DFT calculations suggest that the origin of accelerated ring cleavage is improved frontier molecular orbital overlap in the thiolate-disulfide interchange transition (FIG. 1B). Five to seven-membered cyclic thiosulfinates were synthesized and efficiently cross-linked up to 104-fold faster than their cyclic disulfide precursors; functioned in the presence of biological concentrations of glutathione; and acted as cell-permeable, potent, tolerable, intracellular cross-linkers. In some embodiments, this new class of thiol cross-linkers exhibited click-like attributes including, high yields driven by the enthalpies of disulfide and water formation, orthogonality with common functional groups, water-compatibility, and ring strain-dependence.

The reactions require that binding to lone thiolates be reversible and ideally favorable (FIG. 1A, top). It was reasoned that the high effective concentration ("EC") of cyclic disulfides—i.e., their entropically driven propensity to remain oxidized and cyclic—would enable reversible binding to a single thiolate. Covalent binding of a cyclic disulfide to a thiolate can proceed rapidly by $S_N2$ thiolate-disulfide interchange. This has been utilized for drug cargo delivery—cargos are transported across the cell membrane via reversible cyclic disulfide binding to the transferrin receptor Cys.[24] Importantly, the ring strain-(in particular the C—S—S—C dihedral angle-) dependence of cyclic disulfide reactivity (and EC) is much greater than that of rings composed of period-two elements.[25] In other words, cyclic disulfide reactivity is predictable and highly tunable.

Thus, also provided herein is a method for transporting a molecule of interest across a cell membrane, comprising:
(a) providing a functionalized molecule of interest comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; and
(b) contacting a cell of interest with the functionalized molecule of interest under conditions for the moiety of Formula I to reversibly bind to one or more cell membrane transport proteins,
thereby facilitating transport of the molecule of interest across the cell membrane.

In some embodiments, the cell membrane transport protein is an ATP-powered pump protein, an ion channel protein, or a transporter protein. In some embodiments, the cell membrane transport protein is transferrin receptor.

A cyclic disulfide cannot cross-link dithiolates without an oxidant—an additional two electron oxidation is be required to form the second disulfide bond (FIG. 1A, middle). It was reasoned that if S-oxo-cyclic disulfides (cyclic thiosulfinates) were used, the oxo group could leave as water concomitant to formation of the second disulfide and irreversible cross-link (FIG. 1A, bottom). In summary, nucleophilic attack by thiolate$_A$ upon the cyclic thiosulfinate results in thiolate-disulfide interchange. A terminal sulfenic acid is exposed, which is then be attacked by thiolate$_B$. The sulfenic oxygen is reduced concomitant to oxidative formation of the second disulfide, resulting in a dithiolate cross-link.

Thus, provided herein is a method for covalent coupling of molecules. The method comprises providing a plurality of first molecules comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; and
contacting the plurality of first molecules with a plurality of second molecules comprising at least one thiol functional group,
thereby forming a plurality of covalent bonds between the S or Se atoms of the first molecule and the free thiol groups of the second molecule.

In some embodiments, W and Y are S in Formula I. In these embodiments, the reaction may be generally represented as:

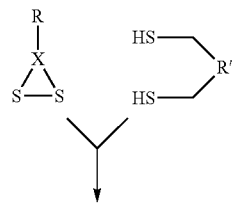

where R and R' are molecules of interest or linker groups attached to molecules of interest.

In some embodiments, W is S and Y is S(O) in Formula I. In these embodiments, the reaction may be represented as:

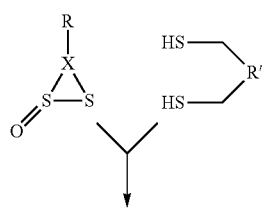

wherein R and R' are molecules of interest or linker groups attached to molecules of interest.

In each of the reactions above, one or more of the sulfur atoms on the group of Formula I can be interchanged with a selenium atom.

The reaction is carried out under conditions to enable a reaction to occur between the thiol groups and the moieties of Formula I, thereby covalently cross-linking the first molecule to the second molecule. In some embodiments, a plurality of covalent bonds between the plurality of the S or Se atoms of the first molecule and the plurality of free thiol groups of the second molecule is formed.

When W and Y are S or Se in Formula I (i.e., a cyclic disulfide or cyclic diselenide), the conditions will generally comprise treating the reaction mixture with an oxidizing agent. Peracids and peroxides may be used for this purpose. A range of oxidizing agents that can be used to oxidize sulfur or selenium are known in the art and can be used. Examples include, but are not limited to: m-chloroperoxybenzoic acid (mCPBA), and hydrogen peroxide.

The conditions may comprise contacting the two molecules of interest with one another in a suitable solvent. Suitable solvents include, but are not limited to, water, DMSO, DMF, methanol, ethanol, propanol, dichloromethane, and mixtures thereof.

In some embodiments, 1,2-dithianes and 1,2-dithiane-1-oxides are used in the polymers, methods of making polymers, and compositions described herein. In some embodiments of the moiety of Formula I as described above and below,
X is $-(CR^1R^2)_n-$, wherein n is an integer selected from the group consisting of 1, 2, 3, 4, 5, 6, 7 and 8; and
each $R^1$ and each $R^2$ on each $CR^1R^2$ group is independently selected from the group consisting of: H, OH, NO$_2$, CN, NH$_2$, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_2$-C$_{12}$heterocycloalkyl, optionally substituted C$_2$-C$_{12}$heterocycloalkenyl, optionally substituted C$_6$-C$_{18}$ aryl, optionally substituted C$_1$-C$_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{12}$heteroalkyloxy, optionally substituted $C_3$-$C_{12}$cycloalkyloxy, optionally substituted $C_3$-$C_{12}$cycloalkenyloxy, optionally substituted $C_1$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $CONR^3R^4$, $NR^3COR^4$, $NR^3COOR^4$, $NR^3SO_2R^4$, $NR^3CONR^3R^4$, and $NR^3R^4$; and wherein each $R^3$ and $R^4$ is independently selected from the group consisting of: H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$—C-18aryl, and optionally substituted $C_1$-$C_{18}$heteroaryl.

In some embodiments of the moiety of Formula I as described above and below, W and Y are S. In some other embodiments, W is S and Y is S(O). In some other embodiments, W and Y are Se. In some other embodiments, W is Se and Y is Se(O). In some other embodiments, W is Se and Y is S. In some other embodiments, W is S and Y is Se. In some other embodiments, W is Se and Y is S(O). In some other embodiments, W is S and Y is Se(O).

In some embodiments as described above and below, W and Y are S, and the moiety of Formula I is represented as follows:

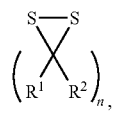

wherein n is an integer from 1 to 8.

In some embodiments as described above and below, W is S and Y is S(O), and the moiety of Formula I is represented as follows:

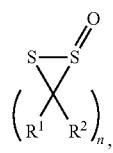

wherein n is an integer from 1 to 8.

In some embodiments as described above and below, W is S and Y is $S(O)_2$, and the moiety of Formula I is represented as follows:

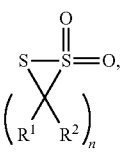

wherein n is an integer from 1 to 8.

In some embodiments of the moiety of Formula I as described above and below, X is —$(CR^1R^2)_n$— where $R^1$ and $R^2$ are as described earlier and n is an integer selected from the group consisting of 3, 4 or 5. In some embodiments, $R^1$ and $R^2$ are H. In some embodiments, the moiety of Formula I is selected from the group consisting of the following formulae (where the wavy line represent the point of attachment to a molecule of interest):

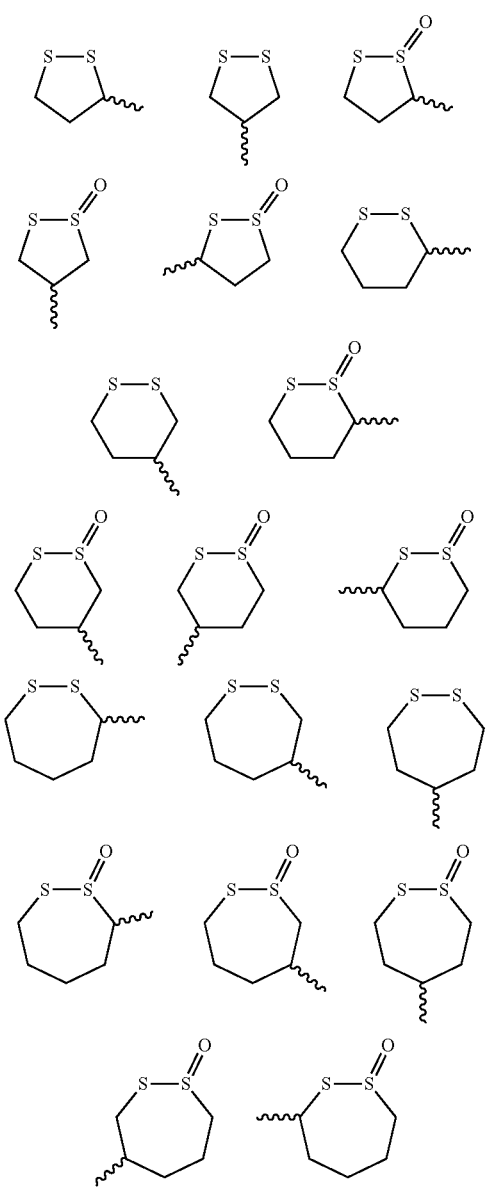

In some embodiments of the moiety of Formula I as described above and below, X is —$(CR^1R^2)_n$— where $R^1$ and $R^2$ are as described earlier and n is an integer selected from the group consisting of 3, 4, 5, 6, or 7. In some embodiments, the moiety of Formula I is selected from the group consisting of:

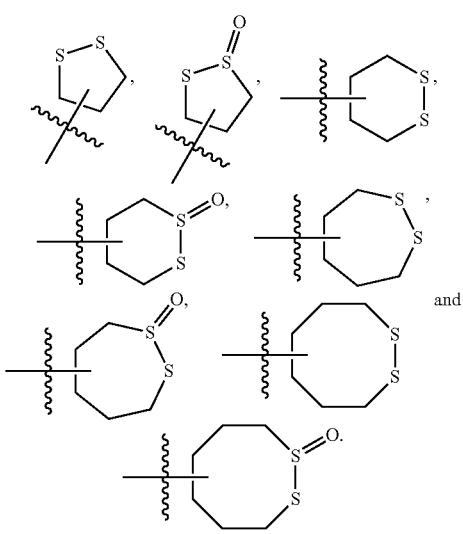

In some embodiments, the moiety of Formula I is selected from the group consisting of:

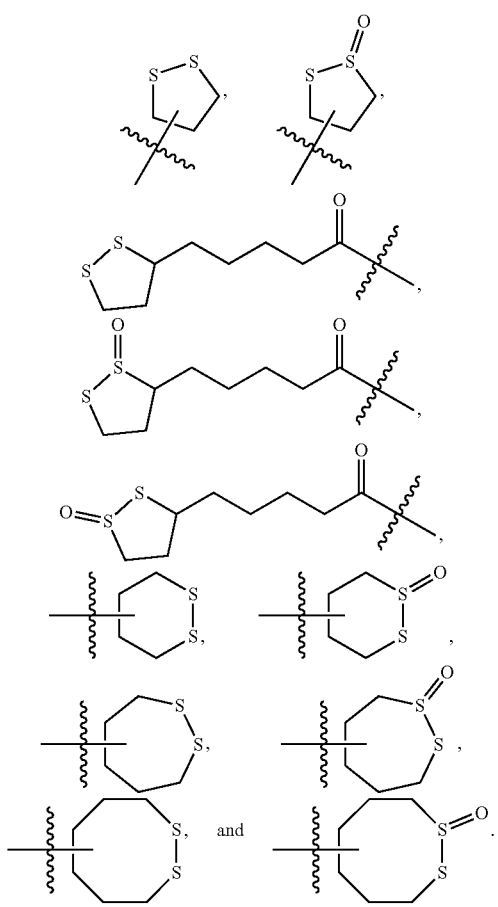

In some embodiments of the moiety of Formula I as described above and below, each $R^1$ and each $R^2$ on each $CR^1R^2$ group is independently selected from the group consisting of H, OH, $NO_2$, CN, $NH_2$, optionally substituted $C_1$-$C_{12}$alkyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_1$-$C_{12}$alkyloxy, optionally substituted $C_2$-$C_{12}$heteroalkyloxy, optionally substituted $C_3$-$C_{12}$cycloalkyloxy, and optionally substituted $C_1$-$C_{12}$heterocycloalkyloxy.

In some embodiments of the moiety of Formula I as described above and below, each $R^1$ and each $R^2$ on each $CR^1R^2$ group is independently selected from the group consisting of H, OH, $NO_2$, CN, $NH_2$, optionally substituted $C_1$-$C_{12}$alkyl, optionally substituted $C_3$-$C_{12}$cycloalkyl, optionally substituted $C_1$-$C_{12}$alkyloxy, and optionally substituted $C_3$-$C_{12}$cycloalkyloxy.

In some embodiments as described above and below, the heterocycle comprising a moiety of Formula I is selected from the group consisting of:

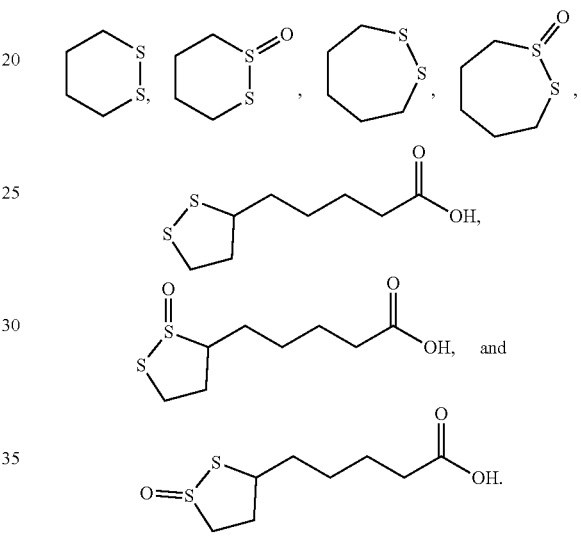

In some embodiments of the moiety of Formula I as described above and below, one or more of the sulfur (S) atoms in the structures above could be interchanged with a selenium (Se) atom, and the resultant structures are also contemplated by the present disclosure.

In some embodiments, the methods and materials described herein are used in "click" chemical reactions. For example, the pairing of the group Formula I and the dithiol (or dithiolate) can replace the azide-alkyne pair and/or the tetrazine-alkene/alkyne pairs used in known click chemical reactions. In some embodiments, the molecule used in the methods described herein comprises a moiety selected from the group consisting of, but not limited to: dyes (e.g., fluorescent dyes, non-fluorescent dyes, quencher dyes); tags (e.g., biotin, FLAG tag); bifunctional reagents; trifunctional reagents; PEGylation reagents; biomolecules (e.g., nucleotides, nucleosides, amino acids, RNA, DNA, peptides, proteins, monosaccharides, polysaccharides); and substrates (e.g., agarose, magnetic beads).

In some embodiments, the methods and materials described herein are regiospecific. In some embodiments, the methods and materials described herein are stereospecific. In some embodiments, the methods and materials described herein produce or represent a single isomer. In some embodiments, the methods and materials described herein produce or represent a mixture of isomers.

The methods and materials described herein can also be used to form dendrimers. In the work of Fang[26], a cyclic disulfide was reduced prior to use and then thiol-ene cross-linkers were used. In contrast, in the present methods the use of oxo cyclic disulfides in place of the cyclic disulfide are cross-linked using molecules with (bifunctional) pair of dithiols. Alternatively, the cyclic disulfide could be reduced to a dithiol, and then reacted with (for example) a homobifunctional cyclic thiosulfinate cross-linker (or more slowly with homobifunctional cyclic disulfide cross-linkers). Alternatively, the cyclic disulfide above could be replaced by a monothiol, and two such molecules could be cross-linked with a single cyclic disulfide or cyclic thiosulfinate. In some embodiments, a cyclic disulfide is used in combination with an oxidizing agent.

In addition, the methods and materials described herein can also be used in cosmetic treatments. Keratin-containing materials consists of many long protein chains that are bound to each other via 1) hydrogen bonding, 2) salt bridges between acid and base groups, and 3) disulfide bonds. Disulfide bonds in keratin-containing materials are broken at a slightly alkaline pH of 8.5, due to heating or use of various reducing treatments. For keratin-containing material treatment, the methods and materials described herein can be used to treat keratin-containing materials by cross-linking the free thiol groups in keratin-containing materials. For example, the compound of Formula I may be attached to a hair treatment agent, such as a colorant, a therapeutic agent or a cosmetic agent, and hair containing broken disulfide bonds may be treated with a composition containing the hair treatment agent to thereby cross link the thiol groups and/or covalently attend the hair treatment agent to the hair.

In addition, in vivo thiol cross-linking using the methods described herein can be used as a strategy for pharmacological protein stabilization, and a long-sought, non-inhibitory alternative to stabilization with substrate analogues.[11] A number of diseases, including familial Amyotrophic Lateral Sclerosis (fALS), are associated with loss of quaternary structure and protein destabilization (seen with Cu/Zn-superoxide dismutase (SOD1) mutations). Multimer stabilization—exemplified by the substrate/cargo analogue, transthyretin-stabilizing drug tafamidis[12]—is a therapeutic strategy in these diseases. Thiol-ene cross-linkers were used in a proof-of-concept study to demonstrate that cross-linking the thiol pair ($Cys_{111A+B}$, 8 Å apart) on adjacent subunits of SOD1 could stabilize fALS-SOD1 variants by up to 40° C.[8] This approach also rescued the enzymatic activity of inherently inactive fALS SOD1 variants.[8] To determine if this approach was applicable to other proteins, a computational screen of human protein structures was performed. This screen discovered 20 additional multimeric proteins with quaternary structures that could be stabilized by intersubunit cysteine cross-linking including DJ-1, a dimeric protein destabilized by Parkinson's associated mutations.

The present inventors surveyed drugs to identify mechanisms for selective thiol binding that can be tolerated in vivo. One recent approach to drug design is to attach a soft, sometimes finely "tuned" Cys-selective electrophile[10] to a high-affinity binder.[13-14] Unfortunately, as is often the case, the lack of high-affinity SOD1 binders ruled out this structure-based approach. The other mechanism used by thiolate-selective drugs, disulfide bond formation, is the most prevalent and mature (disulfiram/Antabuse treatments began in 1948).[15] Inactive prodrugs are transformed into thiols, which, after spontaneous oxidation, form long-lived disulfide bonds between the drug metabolite's sulfenic acid and a target protein's cysteine thiolate. Some drugs form disulfides with enzyme active site Cys (e.g., disulfiram[16]) and others with allosteric Cys (e.g., omeprazole/Prilosec,[17] prasugrel/Effiant,[18] etc.). Unfortunately, the strategy of binding two of these drugs to create a bifunctional cross-linker would not result in a tool that could avoid dead-end modifications.

In some embodiments, the heterocycles comprising a moiety of Formula I disclosed herein form transient bonds. In some embodiments, the heterocycles avoid dead-end modifications without additional molecules. In some embodiments, the heterocycles are cyclic disulfides or cyclic thiosulfinates. Cyclic disulfides are the only thiolate-selective scaffold that the inventors are aware of that can form transient bonds (i.e., can avoid dead-end modifications without the aid of other molecules). Cyclic disulfide chemistry was extensively characterized in a series of publications by the Whitesides group.[19-21] These studies demonstrated the high effective concentration (EC—i.e., the entropically-driven propensity to remain oxidized and cyclic; specifically the $K_{eq}$ between a dithiol forming a cyclic disulfide and a dialkyl disulfide forming two thiols) of cyclic disulfides results in transient binding to lone thiols. Moreover, the $K_{eq}$ of cyclic disulfide binding to lone thiols (i.e., "$K_{eq}$ dead-end") is highly ring strain-dependent, varying over three orders of magnitude.[19-20] Cyclic disulfide-tethered drug cargos can even be transported—with an efficiency that varies with ring strain—across the cell membrane via reversible binding to a transferrin receptor Cys.[22,27] Cyclic disulfides can be tolerated at doses up to 5 g/day/person and have an $LD_{50}$ in the range of ethanol, fructose, and sodium chloride.

The present inventors postulated that cyclic disulfides could cross-link thiol pairs while minimizing dead-end Cys modifications. A reversible $S_N2$-type attack of a Cys thiolate upon a cyclic disulfide would result in thiolate-disulfide interchange concomitant to ring opening to form a terminal thiolate. If this terminal thiolate was within binding distance of a sulfenate (i.e., oxidized Cys), a cross-link could form by their condensation to a disulfide bond (FIG. 1A, Mechanism II).[28] Otherwise, the cyclic disulfide would be released by the reverse (thiolate-disulfide interchange) reaction (FIG. 1A, Mechanism I). Furthermore, if mono-S-oxo cyclic disulfides (cyclic thiosulfinates) were used instead, thiolate oxidation, the slowest step of the cross-linking reaction sequence, would not be required (FIG. 1A, Mechanism III). Instead, thiolate-disulfide interchange with a cyclic thiosulfinate would lead directly to a disulfide-bound terminal sulfenic acid, which would rapidly form a cross-link by condensing with the second, nearby thiolate, releasing water.[28] Thiolate-disulfide interchange proceeds through a linear trisulfide-like intermediate comprised of nucleophilic-($S_n$), center-($S_c$), and leaving group-($S_l$) sulfurs with Brønstead coefficients (β) of ~0.5, −0.3, and −0.7, respectively.[20,29] The Brøstead coefficients of −0.7 and −0.3 for the leaving group and central sulfur, respectively, and our quantum mechanical calculations (FIG. 1B) imply that the rate of thiolate-disulfide interchange is highly sensitive and inversely proportional to the $pK_a$ of $S_1$. DFT calculations were used to understand the origins of the nearly 110-fold reactivity increase of 1 towards lone thiolates over 5 and the observed reversibility. A conformational search was performed on the starting materials, transition structures, and intermediates. Glutathione was represented as methyl thiolate to reduce the conformational search space and computation time.

Figure 12:
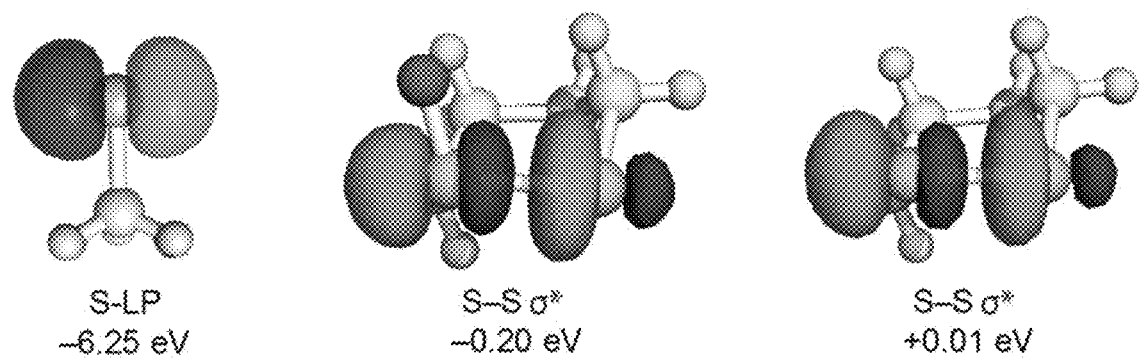
FIG. 12. The energies of the HOMO and LUMOs of $MeS^-$, 1,2-dithiane, and 1,2-dithiane-1-oxide, respectively. Computed using M06-2X/6-311++G(d,p) IEF-$PCM^{H2O}$// M06-2X/6-31+G(d,p).

The 2.9 kcal mol$^{-1}$ lower activation free energy of TS(1→2b) vs. TS(5→2a) is due to more favorable frontier molecular orbital interactions in the transition state (FIG. 1B). The σ* orbital (FIG. 12) of 1 is 0.21 eV lower in energy than that of 5, thus lowering the energy of TS(1→2b). The ring-opening step for 1 and 5 are endergonic (ΔG=4.6 and 5.4 kcal mol$^{-1}$, respectively) and reversible, consistent with experiments. The formation of the cross-linked product and water is thermodynamically favored, over 130 kcal mol$^{-1}$ lower in free energy than the reactants. Upon ring-opening of 1,2-dithiane, 2a is slowly oxidized (t$_{1/2}$=10 days) to 3a, which is rate-determining and affords the final cross-linked product. The QM results highlight two major implications for the low pK$_a$ sulfenic acid group. First, the nucleophilic attack on the non-oxo-thiosulfinate S, which releases sulfenic acid, is >10-fold faster and therefore more likely than the attack on the more electrophilic sulfinyl sulfur. Second, in addition to eliminating the need for rate-limiting thiol oxidation, thiosulfinates, through the sulfenate intermediate generated, also increase the rate of thiolate-disulfide interchange.

Following the general protocols described herein, a polymer or a dendrimer can also be produced by:
providing a plurality of first monomers comprising at least two thiol functional groups;
contacting the plurality of first monomers with a plurality of first cross-linkers comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring,
under conditions to enable a reaction to occur between the thiol functional groups and the cross-linker, thereby forming the polymer or the dendrimer by covalently cross-linking the monomers via the cross-linkers.

In another aspect, provided herein is a polymer derived from a first monomer and a first cross-linker, wherein
the first monomer comprises at least two thiol functional groups;
the first cross-linker comprises a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring.

In certain embodiments of the preceding Formula I, Y is independently selected from the group consisting of S(O), Se(O), S(O)$_2$ and Se(O).

In some embodiments of the methods and polymers disclosed above and below, the first monomer is selected from the group consisting of a dithiol compound, a trithiol compound, a tetrathiol compound, and a thiomer. In some embodiments, the first monomer is selected from the group consisting of a dithiol compound, a trithiol compound, a tetrathiol compound, a hexathiol compound, and an octathiol compound.

In some embodiments of the methods and polymers disclosed above and below, the first monomer is selected from the group consisting of dithiothreitol (DTT), 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,13-tridecanedithiol, 1,14-tetradecanedithiol, 1,16-hexadecanedithiol, dithiolbutylamine (DTBA), tetra(ethylene glycol) dithiol, hexa(ethylene glycol) dithiol, 2-mercaptoethyl ether, 2,2'-thiodiethanethiol, 2,2'-(ethylenedioxy)diethanethiol, propane-1,2,3-trithiol, trimethylolpropane tris(2-mercaptoacetate), trimethylolpropane tris(3-mercaptoacetate), 3,3',3''-((((1,3,5-triazine-2,4,6-triyl)tris(oxy))tris(propane-3,1-diyl))tris(sulfanediyl))tris(propane-1-thiol), 4,4',4''-((((1,3,5-triazine-2,4,6-triyl)tris(oxy))tris(propane-3,1-diyl))tris(sulfanediyl))-tris(butane-1-thiol), pentaerythrityl tetrathiol, pentaerythritol tetrakis(3-mercaptopropionate), a peptide having a disulfide bond, and a protein having a disulfide bond.

In some embodiments, the first monomer is a peptide having a disulfide bond or a protein having a disulfide bond. In some embodiments, the first monomer is a protein having a disulfide bond.

In some embodiments, the first monomer is copper/zinc superoxide dismutase (SOD1) or DJ-1, which has been implicated in Parkinson's disease. In some embodiments, the first monomer is selected from the group consisting of an SOD1 variant, a DJ-1 variant, an effector caspase (e.g., Caspase-3), and iron-sulfur cluster assembly enzyme (IscU). In some embodiments, the first monomer is SOD1. In some embodiments, the first monomer is a fALS-SOD1 variant. In some embodiments, the first monomer is a DJ-1 variant. In some embodiments, the first monomer is an effector caspase. In some embodiments, the first monomer is Caspase-3. In some embodiments, the first monomer is IscU.

In some embodiments, the first monomer is a keratin-containing material. In some embodiments, the keratin-containing material is selected from the group consisting of hair (including facial hair such as eyebrows, eyelashes, beards, and moustaches), fingernails and toenails. In some embodiments, the keratin-containing material is selected from the group consisting of hair, eyebrows, eyelashes, fingernails and toenails. In some embodiments, the keratin-containing material is hair.

In some embodiments of the methods and polymers disclosed above and below, the first monomer is selected from the group consisting of poly(ethylene glycol) dithiol (PEG-DT, e.g., with average M$_n$ of 1,500), 4 arm-PEG2K—SH, 4 arm-PEG5K-SH, 4 arm-PEG10K—SH, 4 arm-PEG20K—SH, 4-arm poly(ethylene oxide) thiol-terminated, 8 arm-PEG10K—SH (hexaglyerol core), 8 arm-PEG10K—SH (tripentaerythritol core), 8 arm-PEG20K—SH (hexaglyerol core), 8 arm-PEG20K—SH (tripentaerythritol core), and 8-arm poly(ethylene oxide) thiol-terminated. In some embodiments of the methods and polymers disclosed above and below, the first monomer is poly(ethylene glycol) dithiol or polyethylene dithiol.

In certain embodiments of the methods and polymers disclosed above and below, the first monomer comprising at least two thiol functional groups is a polyalkylene dithiol, such as polyethylene dithiol, polypropylene dithiol, etc.

In some embodiments in the methods and polymers disclosed above and below, the first cross-linker comprising a moiety of Formula I stabilizes a first monomer. In some embodiments, the first cross-linker stabilizes a peptide having a disulfide bond or a protein having a disulfide bond. In some embodiments, the first cross-linker stabilizes a fALS-SOD1 variant or a DJ-1 variant. In some embodiments, the unfolding temperature of the first monomer is increased. In some embodiments, the unfolding temperature is increased by at least 2° C., at least 5° C., at least 10° C., at least 15° C., at least 20° C., at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., or at least 100° C. In some embodiments, the unfolding temperature is increased by an amount selected from the group consisting of about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., and about 110° C.

In some embodiments in the methods and polymers disclosed above and below, the first cross-linker comprising a moiety of Formula I suppresses aggregation of a first monomer. In some embodiments, the first cross-linker suppresses aggregation of a peptide having a disulfide bond or a protein having a disulfide bond. In some embodiments, the first cross-linker suppresses aggregation of a fALS-SOD1 variant.

In some embodiments in the methods and polymers disclosed above and below, the first cross-linker comprising a moiety of Formula I inhibits apoptosis. In some embodiments, the first cross-linker cross-links an effector caspase.

In some embodiments in the methods and polymers disclosed above and below, the first cross-linker comprising a moiety of Formula I causes ferroptosis. In some embodiments, the first cross-linker kills a plurality of cancer cells. In some embodiments, the first cross-linker cross-links IscU.

In some embodiments in the methods and polymers disclosed above and below, the first cross-linker comprising a moiety of Formula I is used in a method for treating a keratin-containing material. In some embodiments, the first cross-linker cross-links the keratin-containing material. In some embodiments, the method for treating a keratin-containing material, comprises:
i) providing a plurality of first monomers, wherein the first monomer is a keratin-containing material sample comprising a plurality of disulfide bonds;
ii) applying to the keratin-containing material sample for a period of time a mixture, comprising a reducing agent in a concentration of about 0.1% by weight to about 15% by weight, thereby producing a reduced keratin-containing material sample, wherein the reduced keratin-containing material sample comprises a plurality of free thiol groups; and
iii) applying a first cross-linker to the reduced keratin-containing material sample, wherein the first cross-linker comprises a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring,
thereby forming a plurality of covalent bonds between the free thiol groups and the first cross-linkers.

In some embodiments, the reducing agent is selected from the group consisting of ammonium thioglycolate, L-cysteine, glutathione, ascorbic acid, beta-mercaptoethanol, 2-mercaptoethylamine, 2-mercaptoethylamine hydrochloride, dithiothreitol (DTT), thiolactic acid, thiosalicylic acid, tris-2-carboxyethylphospine hydrochloride (TCEP), sodium hydrosulfite, sodium thiosulfate, potassium disulfite, sodium disulfite, sodium bisulfate, sodium bisulfite, ammonium bisulfite, thioglycolic acid, calcium thioglycolate, potassium thioglycolate, sodium thioglycolate, cysteine hydrochloride, ammonium thiolactate, thioglycerin, mercaptoprpionic acid, glycerol thioglycolate and dithiolbutylamine (DTBA). In some embodiments, the reducing agent is selected from the group consisting of ammonium thioglycolate, L-cysteine, glutathione, beta-mercaptoethanol, 2-mercaptoethylamine, DTT, thiolactic acid, TCEP, DTBA, sodium hydrosulfite, and sodium thiosulfate. In some embodiments, the reducing agent is selected from the group consisting of ammonium thioglycolate, L-cysteine, glutathione, and thiolactic acid. In some embodiments, the reducing agent is ammonium thioglycolate or L-cysteine. In some embodiments, the reducing agent is ammonium thioglycolate. In some embodiments, the reducing agent is beta-mercaptoethanol.

In some embodiments, the reducing agent is a mixture comprising a first cross-linker comprising a moiety of Formula I. In some embodiments, the reducing agent is a mixture of cyclic disulfides and cyclic thiosulfinate. In some embodiments, the method for treating a keratin-containing material, comprises:
i) providing a plurality of first monomers, wherein the first monomer is a keratin-containing material sample comprising a plurality of disulfide bonds;
ii) applying to the keratin-containing material sample for a period of time a mixture, comprising a first cross-linker, wherein the first cross-linker comprises a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring,
thereby forming a plurality of free thiol groups which react with the first cross-linkers to form a plurality of covalent bonds between the free thiol groups and the first cross-linkers.

In some embodiments of the methods and polymers disclosed above and below, the first cross-linker is selected from the group consisting of 1-oxo-1,2-dithiane, 1-oxo-1,2-dithiepane, and 1-oxo-1,2-dithiocane. In some embodiments, the first cross-linker is 1-oxo-1,2-dithiane.

In some embodiments of the methods and polymers disclosed above and below, the ratio of the first monomer to the first cross-linker is from about 1:10 to about 10:1. In some embodiments, the ratio of the first monomer to the first cross-linker is selected from about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, and about 10:1.

In certain embodiments of the methods disclosed above and below, the method further comprises contacting the plurality of first cross-linkers with a plurality of second monomers comprising at least two thiol functional groups.

In some embodiments of polymers disclosed above and below, the polymer derived from a first monomer, a first cross-linker, and a second monomer.

In some embodiments of the methods and polymers disclosed above and below, the second monomer is trithiol compound or a tetrathiol compound, such as trithiocyanuric acid, trimethylolpropane tris(3-mercaptopropionate), and pentaerythritol tetra(3-mercaptopropionate). In some embodiments, the second monomer is selected from the group consisting of trithiocyanuric acid, trimethylolpropane tris(3-mercaptopropionate), and pentaerythritol tetra(3-mercaptopropionate).

In some embodiments of the methods disclosed above and below, the method further comprises contacting the plurality of first cross-linkers with a plurality of second cross-linkers comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring.

In some embodiments of polymers disclosed above and below, the polymer derived from a first monomer, a first cross-linker, and a second cross-linker.

In some embodiments of the methods and polymers disclosed above and below, the plurality of first cross-linkers is different from the plurality of second cross-linkers. In some embodiments, the ratio of the plurality of first cross-linkers to the ratio of the plurality of second cross-linkers is from about 1:10 to about 10:1. In some embodiments, the ratio is selected from about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, and about 10:1. In some embodiments, the plurality of first cross-linkers comprise a cyclic disulfide. In some embodiments, first cross-linkers comprise a cyclic thiosulfinate. In some embodiments, the plurality of second cross-linkers comprise a cyclic disulfide. In some embodiments, the plurality of second cross-linkers comprise a cyclic thiosulfinate.

In another aspect, the present disclosure provides a method of coating a surface of an object, a device, or an assembly, comprising the steps of:
(a) providing a surface of an object, a device, or an assembly;
(b) contacting the surface with a plurality of first molecules comprising a reactive moiety and a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring;
thereby forming a plurality of covalent bonds between the surface and the reactive moieties of the first molecule to form a first monolayer.

In some embodiments of the methods of coating a surface, W is S and Y is S or S(O). In some embodiments, the surface is reductive. In some embodiments, the reactive moiety is a thiol or a thiosulfinate.

In some embodiments, the method of coating a surface further comprises
(c) contacting the monolayer with a second molecule comprising at least one thiol functional group, thereby forming a first bilayer, wherein a plurality of covalent bonds are formed between the S or Se atoms of the first molecule and the free thiol groups of the second molecule.

In some embodiments of the methods of coating a surface, the second molecule is a monothiol compound. In some embodiments, the second molecule is selected from the group consisting of (11-mercaptoundecyl)-N,N,N-trimethylammonium bromide, (11-mercaptoundecyl)hexa(ethylene glycol), (11-mercaptoundecyl)tetra(ethylene glycol), 1-(11-mercaptoundecyl)imidazole, 1-mercapto-2-propanol, 11-(1H-pyrrol-1-yl)undecane-1-thiol, 11-(ferrocenyl)undecanethiol, 11-amino-1-undecanethiol hydrochloride, 11-azido-1-undecanethiol, 11-mercapto-1-undecanol, 11-mercaptoundecanamide, 11-mercaptoundecanoic acid, 11-mercaptoundecylhydroquinone, 11-mercaptoundecylphos-phonic acid, 12-mercaptododecanoic acid, 16-amino-1-hexadecanethiol hydrochloride, 16-mercaptohexadecanamide, 16-mercaptohexadecanoic acid, 3-amino-1-propanethiol hydrochloride, 3-chloro-1-propanethiol, 3-mercapto-1-propanol, 3-mercaptopropionic acid, 4-mercapto-1-butanol, 6-(ferrocenyl)-hexanethiol, 6-amino-1-hexanethiol hydrochloride, 6-mercapto-1-hexanol, 6-mercaptohexanoic acid, 8-amino-1-octanethiol hydrochloride, 8-mercapto-1-octanol, 8-mercaptooctanoic acid, 9-mercapto-1-nonanol, triethylene glycol mono-11-mercaptoundecyl ether, 1-mercaptosuccinic acid, a peptide having a cysteine residue, a protein having a cysteine residue, cysteamine, 1-thiohexitol, poly(ethylene glycol) 2-mercaptoethyl ether acetic acid, poly(ethylene glycol) methyl ether thiol, 1-thioglycerol, 2-naphthalenethiol, biphenyl-4-thiol, 3-amino-1,2,4-triazole-5-thiol, 5-(trifluoromethyl)pyridine-2-thiol, 1-[2-(dimethylamino)ethyl]-1H-tetrazole-5-thiol, 1-propanethiol, 1-butanethiol, 1-pentanethiol, 1-hexanethiol, 1-octanethiol, 3,3,4,4,5,5,6,6,7,7,8,8,8-tridecafluoro-1-octanethiol, and γ-Glu-Cys.

In some embodiments of the methods of coating a surface, the second molecule is selected from the group consisting of a dithiol compound, a trithiol compound, a tetrathiol compound, and a thiomer. In some embodiments, the second molecule is selected from the group consisting of a dithiol compound, a trithiol compound, a tetrathiol compound, a hexathiol compound, and an octathiol compound.

In some embodiments of the methods of coating a surface, the second molecule is selected from the group consisting of dithiothreitol (DTT), 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,13-tridecanedithiol, 1,14-tetradecanedithiol, 1,16-hexadecanedithiol, dithiolbutylamine (DTBA), tetra(ethylene glycol) dithiol, hexa(ethylene glycol) dithiol, 2-mercaptoethyl ether, 2,2'-thiodiethanethiol, 2,2'-(ethylenedioxy)diethanethiol, propane-1,2,3-trithiol, trimethylolpropane tris(2-mercaptoacetate), trimethylolpropane tris(3-mercaptoacetate), 3,3',3"-((((1,3,5-triazine-2,4,6-triyl)tris(oxy))tris(propane-3,1-diyl))tris(sulfanediyl))tris(propane-1-thiol), 4,4',4"-((((1,3,5-triazine-2,4,6-triyl)tris(oxy))tris(propane-3,1-diyl))tris(sulfanediyl))tris(butane-1-thiol), pentaerythrityl tetrathiol, pentaerythritol tetrakis(3-mercaptopropionate), a peptide having a disulfide bond, and a protein having a disulfide bond. In some embodiments, the second molecule is a peptide having a disulfide bond or a protein having a disulfide bond. In some embodiments, the second molecule is a protein having a disulfide bond. In some embodiments, the second molecule is copper/zinc superoxide dismutase (SOD1) or DJ-1, which has been implicated in Parkinson's disease. In some embodiments, the second molecule is SOD1.

In some embodiments of the methods of coating a surface, the second molecule is selected from the group consisting of 4 arm-PEG2K—SH, 4 arm-PEG5K-SH, 4 arm-PEG10K—SH, 4 arm-PEG20K—SH, 4-arm poly(ethylene oxide) thiol-terminated, 8 arm-PEG10K—SH (hexaglyerol core), 8 arm-PEG10K—SH (tripentaerythritol core), 8 arm-PEG20K—SH (hexaglyerol core), 8 arm-PEG20K—SH (tripentaerythritol core), and 8-arm poly(ethylene oxide) thiol-terminated.

In certain embodiments of the methods of coating a surface, the second molecule is a polyalkylene dithiol, such as polyethylene dithiol, polypropylene dithiol, etc.

In certain embodiments of the methods of coating a surface, the second molecule is a trithiol compound or a tetrathiol compound, such as trithiocyanuric acid, trimethylolpropane tris(3-mercaptopropionate), and pentaerythritol tetra(3-mercaptopropionate).

In some embodiments, the method of coating a surface further comprises
(d) applying an electrical potential, thereby reducing the covalent bonds, thus forming a second monolayer.

In some embodiments, the method of coating a surface further comprises
(e) providing an aqueous mixture comprising water and a plurality of metal ions, thereby forming a complex, comprising a plurality of metal-chelating groups of the second monolayer chelated to the plurality of metal ions, thus forming a second bilayer.

In some embodiments, the method of coating a surface further comprises
(f) contacting the second bilayer with a plurality of third molecules comprising a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring;
thereby forming a trilayer, wherein the plurality of third molecules are chelated to the plurality of metal ions.

In another aspect, provided herein is a composition, wherein the composition comprises a substrate and a coating material, wherein the coating material comprises a first monolayer comprising a plurality of moieties of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring; and
the coating material is covalently bonded to the substrate.

In some embodiments of the composition, the first monolayer comprises a plurality of moieties selected from the group consisting of

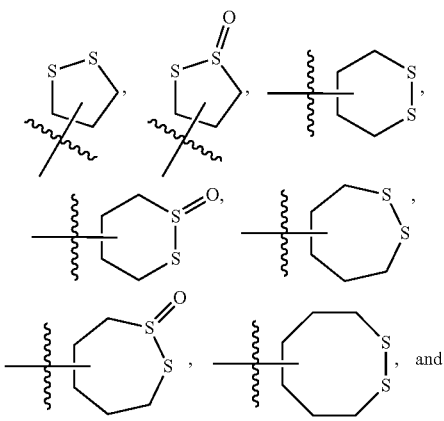

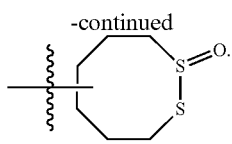

In some embodiments, the first monolayer comprises a plurality of moieties selected from the group consisting of

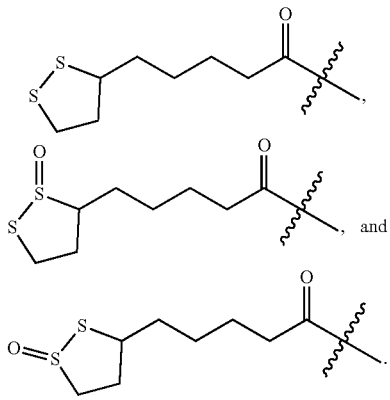

In some embodiments of the composition, the coating material comprises a first bilayer comprising a polymer derived from the moieties of Formula I and a plurality of first monomers comprising at least one thiol functional group, wherein a plurality of covalent bonds are formed between the S or Se atoms of the plurality of moieties and the free thiol groups of the first monomer.

In some embodiments of the composition, the coating material comprises a second monolayer comprising a reduced form of the plurality of moieties of Formula I.

In some embodiments of the composition, the coating material comprises a second bilayer comprising a plurality of metal-chelating groups of the second monolayer chelated to a plurality of metal ions.

In some embodiments of the methods of coating or coating compositions, the plurality of metal-chelating groups are S atoms. In some embodiments, the plurality of metal-chelating groups are Se atoms.

In some embodiments of the methods of coating or coating compositions, the plurality of metal ions are a plurality of metal cations.

In some embodiments of the methods of coating or coating compositions, the metal cation has a charge of +1. In some embodiments, the metal cation is a cation of Ag or Au.

In some embodiments of the methods of coating or coating compositions, the metal cation has a charge of +2. In some embodiments, the metal cation is a cation of Ca, Cd, Co, Cr, Cu, Er, Fe, Hg, Mg, Mn, Nb, Ni, Pb, Pd, Sc, Sn, Sr, V, or Zn. In some embodiments, the metal cation is a cation of Cd, Co, Cr, Cu, Fe, Hg, Mn, Nb, Ni, Pb, Pd, Sn, Sr, V, or Zn.

In some embodiments of the methods of coating or coating compositions, the metal cation has a charge of +3. In some embodiments, the metal cation is a cation of Au, Ce, Dy, Er, Eu, Fe, Gd, Ho, La, Lu, Nb, Nd, Pm, Pr, Sm, Tb, Tm, or Yb. In some embodiments, the metal cation is a cation of Ce, Dy, Er, Eu, Gd, Ho, La, Lu, Nd, Pm, Pr, Sm, Tb, Tm, or Yb. In some embodiments, the metal cation is a cation of Au, Fe, or Gd. In some embodiments, the metal cation is a cation of Au or Fe.

In some embodiments of the composition, the coating material comprises a trilayer further comprising a plurality of third molecules chelated to the plurality of metal ions, wherein the third molecules comprise a moiety of Formula I:

Formula I wherein
W is independently selected from the group consisting of S and Se;
Y is independently selected from the group consisting of S, Se, S(O), Se(O), S(O)$_2$ and Se(O)$_2$; and
X together with W and Y forms a substituted or unsubstituted 3-10-membered heterocyclic ring.

In summary, cyclic disulfide and cyclic diselenide reactivity, including reversible binding to lone thiols, is predictable and highly tunable. Cyclic thiosulfinate, cyclic thioselenoxide and cyclic selenosulfinate cross-linkers have potential as:

1) A less toxic alternative to Cys specific diene cross-linkers and phenylarsine oxide cross-linkers, which can both react with monothiols,[33]
2) Probes for proteinaceous Cys-dithiolates, which perform essential in vivo functions and often serve as metal and metallocofactor ligands,[34-36]
3) Inter-functional group distance measurement tools,
4) Biocompatible templates for higher order structures in polymer synthesis, and
5) Cellular thiol pair cross-linkers.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

Throughout the specification and the claims, unless the context requires otherwise, the words "comprise" and "include" and variations such as "comprising" and "including" will be understood to imply the inclusion of a stated integer or group of integers, but not the exclusion of any other integer or group of integers.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Typically, a straight chained or branched alkenyl group has from 1 to about 20 carbon atoms, preferably from 1 to about 10 unless otherwise defined. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, pentyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. Co alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "arylthio", as used herein, refers to a thiol group substituted with an alkyl group and may be represented by the general formula arylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Typically, a straight chained or branched alkynyl group has from 1 to about 20 carbon atoms, preferably from 1 to about 10 unless otherwise defined. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

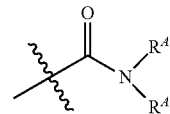

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

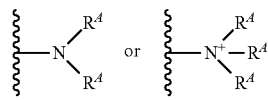

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 20-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

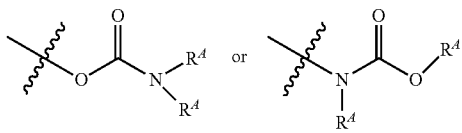

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. Preferably, a carbocyclic group has from 3 to 20 carbon atoms. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Preferably, a cycloalkyl group has from 3 to 20 carbon atoms. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate", as used herein, refers to a group —OCO$_2$—R$^A$, wherein R$^A$ represents a hydrocarbyl group.

The term "carboxy", as used herein, refers to a group represented by the formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom, wherein that carbon atom does not have a =O or =S substituent. Hydrocarbyls may optionally include heteroatoms. Hydrocarbyl groups include, but are not limited to, alkyl, alkenyl, alkynyl, alkoxyalkyl, aminoalkyl, aralkyl, aryl, aralkyl, carbocyclyl, cycloalkyl, carbocyclylalkyl, heteroaralkyl, heteroaryl groups bonded through a carbon atom, heterocyclyl groups bonded through a carbon atom, heterocyclylakyl, or hydroxyalkyl. Thus, groups like methyl, ethoxyethyl, 2-pyridyl, and trifluoromethyl are hydrocarbyl groups, but substituents such as acetyl (which has a =O substituent on the linking carbon) and ethoxy (which is linked through oxygen, not carbon) are not.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are six or fewer non-hydrogen atoms in the substituent. A "lower alkyl", for example, refers to an alkyl group that contains six or fewer carbon atoms. In some embodiments, the alkyl group has from 1 to 6 carbon atoms, from 1 to 4 carbon atoms, or from 1 to 3 carbon atoms. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

In the phrase "poly(meta-phenylene oxides)", the term "phenylene" refers inclusively to 6-membered aryl or 6-membered heteroaryl moieties. Exemplary poly(meta-phenylene oxides) are described in the first through twentieth aspects of the present disclosure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfonate" is art-recognized and refers to the group $SO_3H$, or a pharmaceutically acceptable salt thereof.

The term "sulfone" is art-recognized and refers to the group $—S(O)_2—R^A$, wherein $R^A$ represents a hydrocarbyl.

The term "thioether", as used herein, is equivalent to an ether, wherein the oxygen is replaced with a sulfur.

EXAMPLES

Materials and Instrumentation 1,4-butanedithiol used in the synthesis of both 1,2-dithiane and 1,2-dithiane-1-oxide was purchased through TCI America (Portland, OR, USA). All buffer components and solvents (including ESI solvents) used in the kinetic assay experiments were purchased through Fisher Scientific (Hampton, New Hampshire, USA) except formic acid which was purchased through Sigma-Aldrich (St. Louis, Missouri, USA). Incubation of samples was done in an Eppendorf Thermomixer R (Hauppauge, New York, USA). All cell culture ingredients were purchased through ATCC (Manassas, Virginia, USA). Cells were incubated in a ThermoFisher Isotemp incubator (Waltham, Massachusetts, USA). SDS Page was performed using a MiniProtean electrophoresis chamber (Hep G2 experiments) and Criterion electrophoresis chamber (HeLa experiments) from Bio Rad (Hercules, California, USA). Cu/Zn SOD polyclonal antibody was purchased through Enzo (Farmingdale, New York, USA). Pierce Secondary antibody was purchased through Thermo Scientific (Waltham, Massachusetts, USA). Membranes were imagined on a Bio Rad ChemiDoc MP (Hercules, California, USA). Mass spectra for kinetic assays was acquired on a Bruker Solarix XR FT-ICR mass spectrometer with an electrospray ionization source and a 9.4 Tesla magnet. Acquired data was analyzed and processed using Bruker Daltronics DataAnalysis 4.4.102 software (Billerica, Massachusetts, USA). $^1H$ NMR spectra were recorded at ambient temperature on a Varian Mercury NMR spectrometer (Palo Alto, California, USA) operating at 400 MHz in the solvent indicated with the signal of the residual solvent ($CHCl_3$ δ 7.26 ppm) as internal standard. $^{13}C$ NMR spectra were recorded with $^1H$ decoupled observation at ambient temperature on a Varian NMR spectrometer operating at 100 MHz in the solvent indicated with the signal of the residual solvent ($CHCl_3$ δ 77.16 ppm) as internal standard. Data are reported as follows: chemical shift, multiplicity (m=multiplet, dt=doublet of triplets, td=triplet of doublets, dtt=doublet of triplet of triplets), integration and coupling constant (Hz). Thin-layer chromatography (TLC) was performed with silica gel 60 F254 pre-coated plates and visualized with exposure to UV light (254 nm) or by potassium permanganate stain (KMnO4) followed by heating. Phenylarsine oxide was purchased through Sigma-Aldrich (St. Louis, Missouri, USA). SOD1 (WT and C111S) yeast expression vectors were kindly provided by P. J Hart (The University of Texas Health Science Center). Both phenyl-sepharose hydrophobic interaction chromatography column and Mono Q 10/100 anion exchange chromatography column was purchased through GE Life Sciences (Piscataway, New Jersey, USA) and protein purification was performed on an Akta Fast Protein Liquid Chromatography (FPLC) (Piscataway, New Jersey, USA). LC-MS data was collected on a Bruker HCT Ultra ion trap (Billerica, Massachusetts, USA).

Methods

Synthesis of 1,2-dithiane

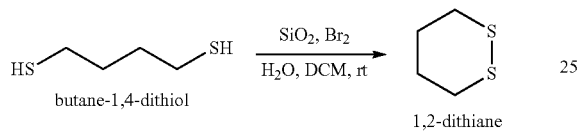

Preparation of 1,2-dithiane was adapted from a known literature procedure.[37] Silica gel (40-60 μm particle size, 60 Å pore size, 41 g) was added to a round bottom flask and distilled water (102 mL) was added slowly with rigorous stirring until a uniform suspension had formed. Dichloromethane (200 mL) and 1,4-butanedithiol (2.00 g, 16.4 mmol, 1 equiv) were added to the suspension while stirring. A solution of $Br_2$ (2.88 g, 18 mmol, 1.10 equiv) in dichloromethane (16 mL) was added dropwise to the off-white suspension while stirring vigorously. The reaction mixture was stirred for 5 minutes, and reaction completion was confirmed by TLC analysis. The reaction mixture was filtered over celite into a flask containing a stirred solution of 1.25 M NaOH (12 mL). The colorless organic phase was removed, washed with distilled water (3×50 mL) and dried over sodium sulfate. The solvent was removed under reduced pressure and the crude product crystallized from hexanes at −20° C. to yield 1,2-dithiane as a white crystalline solid (1.63 g, 83%). $R_f$=0.80 (5:1 hexanes:EtOAc); $^1$H NMR (400 MHz, $CDCl_3$, δ): 1.97 (bs, 4H), 2.85 (bs, 4H); $^{13}$C NMR (100 MHz, $CDCl_3$, δ): 27.9, 33.5. mp 29-32° C. (lit. 28-30° C.).[37]

Synthesis of 1,2-dithiane-1-oxide

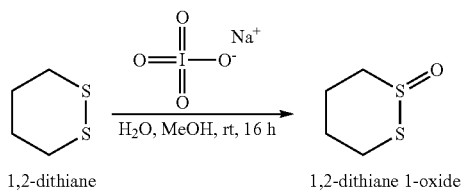 [SMILES: C1CCSSC1 ; [O-][I+3]([O-])([O-])[O-] ; [Na+] ; O=S1CCCCS1]

Preparation of 1,2-dithiane-1-oxide was adapted from a known literature procedure.[37] A solution of sodium periodate (843 mg, 3.94 mmol, 1.10 equiv) in water (64 mL) was added dropwise to a stirred solution of 1,2-dithiane (431 mg, 3.58 mmol, 1 equiv) in methanol (193 mL) at 0° C. The reaction mixture was stirred 16 h, and reaction completion was confirmed by TLC analysis. The white slurry warmed to room temperature, filtered over celite, and the filtrate was concentrated under reduced pressure. The remaining solution was diluted with chloroform (40 mL) and transferred to a separatory funnel. A small amount of solid NaCl was added and the aqueous layer was extracted with $CHCl_3$ (3×40 mL). The combined organic layer was dried over sodium sulfate, the solvent removed under reduced pressure, and purified by flash column chromatography on silica gel with 2% $MeOH/CH_2Cl_2$ yielded 1,2-dithiane-1-oxide as a colorless solid (214 mg, 44%). $R_f$=0.33 (2% MeOH/$CH_2Cl_2$); $^1$H NMR (400 MHz, $CDCl_3$, δ): 1.85-1.88 (m, 1H), 1.96-2.06 (dtt, J=13.7, 12.7, 3.0 Hz, 1H), 2.11-2.15 (m, 1H), 2.62-2.71 (m, 2H), 3.04-3.12 (dt, J=13.1, 3.0 Hz, 1H), 3.18-3.23 (td, J=13.3, 3.6 Hz, 1H), 3.62-3.70 (ddd, J=14.5, 12.0, 2.5 Hz, 1H); $^{13}$C NMR (100 MHz, $CDCl_3$, δ): 15.3, 23.5, 25.8, 51.9. HRMS-ESI (m/z): $[M+H]^+$ calcd for $C_4H_8OS_2$, 137.00893 Da; found 137.00893 Da. mp 83-86° C. (lit. 85° C.).[37]

Synthesis of 1,2-dithiepane

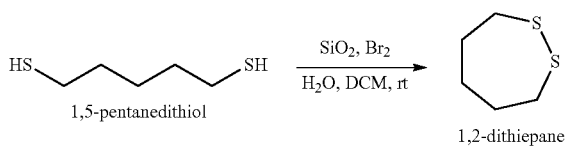 [SMILES: SCCCCCS ; C1CCSSCC1]

Preparation of 1,2-dithiepane was adapted from a known literature procedure.[37] Silica gel (40-60 μm particle size, 60 Å pore size, 46 g) was added to a round bottom flask and distilled water (23 mL) was added slowly with rigorous stirring until a uniform suspension had formed. Dichloromethane (230 mL) and 1,5-pentanedithiol (3.00 g, 22.01 mmol, 1 equiv) were added to the suspension while stirring. A solution of Bra (3.87 g, 24.22 mmol, 1.10 equiv) in dichloromethane (23 mL) was added dropwise to the off-white suspension while stirring vigorously. The reaction mixture was stirred for 5 minutes, and reaction completion was confirmed by TLC analysis. The reaction mixture was filtered over celite into a flask containing a stirred solution of 1.25 M NaOH (110 mL). The colorless organic phase was removed, washed with distilled water (3×70 mL) and dried over sodium sulfate. The solvent was removed under reduced pressure and the crude product purified by flash column chromatography on silica gel with 20:1 Hex/EtOAc yielded 1,2-dithiepane as a clear liquid (2.83 g, 96%). $R_f$=0.82 (9:1 hexanes:EtOAc); $^1$H NMR (400 MHz, $CDCl_3$, δ): 1.75-1.79 (m, 2H), 2.00-2.05 (m, 4H), 2.82-2.84 (t, J=6.3, 4H); $^{13}$C NMR (100 MHz, $CDCl_3$, δ): 26.0, 30.0, 39.2.

Synthesis of 1,2-dithiepane-1-oxide

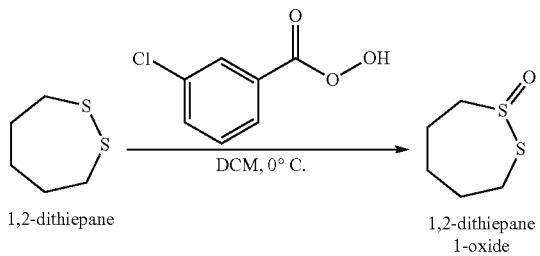 [SMILES: C1CCSSCC1 ; O=C(OO)c1cccc(Cl)c1 ; O=S1CCCCCS1]

1,2-dithiepane → 1,2-dithiepane 1-oxide

Preparation of 1,2-dithiepane was adapted from a known literature procedure for the oxidation of disulfides.[38] mCPBA (73%, 214 mg, 0.909 mmol, 1.07 equiv) was added at 0° C. to a solution of 1,2-dithiepane (114 mg, 0.849 mmol, 1 equiv) in anhydrous dichloromethane (5.5 mL). The solution was stirred in an ice bath for 1 h, then sodium carbonate (1 g) was added and stirred for 30 min at 0° C. The solution was filtered over a celite pad and magnesium sulfate, solvent was removed under reduced pressure and the crude product purified by flash column chromatography on silica gel with 5:1 Hex/EtOAc yielded 1,2-dithiepane-1-oxide as a clear liquid (97 mg, 76%). $R_f$=0.19 (5:1 hexanes:EtOAc); $^1$H NMR (400 MHz, CDCl$_3$, δ): 1.73-1.81 (m, 1H), 1.91-2.02 (m, 4H), 2.09-2.16 (m, 1H), 2.77-2.86 (m, 2H), 3.36-3.41 (dd, J=6.5, 13.8 Hz, 1H), 3.50-3.57 (m, 1H); $^{13}$C NMR (100 MHz, CDCl$_3$, δ): 18.02, 22.31, 26.77, 28.46, 60.56. HRMS-ESI (m/z): [M+H]$^+$ calcd for C$_5$H$_{10}$OS$_2$, 151.024584 Da; found 151.02498 Da.

Synthesis of β-lipoic acid

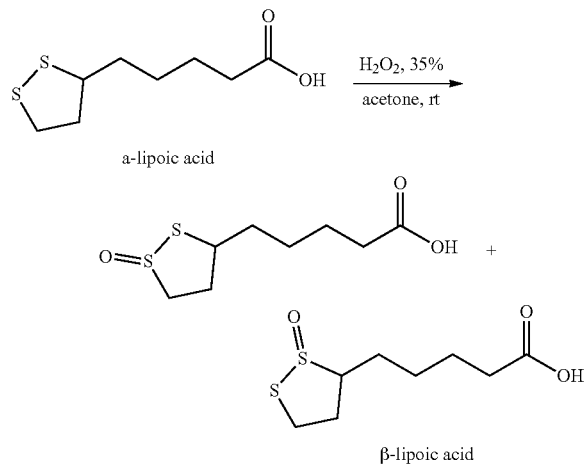

α-lipoic acid → β-lipoic acid

Preparation of β-lipoic acid was adapted from a known literature procedure.[39] Aqueous hydrogen peroxide (0.841 mL, 35% in H2O, 9.77 mmol, 2 equiv) was added to a solution of DL-thioctic acid (α-lipoic acid, 1.01 g, 4.89 mmol, 1 equiv) in acetone (2.5 mL) and allowed to stir for 24 h. Solvent was removed under reduced pressure, diluted with dichloromethane (25 mL) and then added to brine (50 mL). The aqueous layer was extracted with dichloromethane (3×25 mL) and dried over sodium sulfate. The solvent was removed under reduced pressure and purified by flash column chromatography on silica gel with 3% MeOH/CH$_2$Cl$_2$, 0.1% AcOH yielded beta-lipoic acid as a colorless oil (418 mg, 39%). Rf=0.46 (8% MeOH/CH$_2$Cl$_2$, 0.1% AcOH). $^1$H-NMR spectrum and $^{13}$C-NMR data matched those reported by others[39-40] for a mixture of all four stereo- and regioisomers: the $^1$H-NMR and $^{13}$C-NMR chemical shifts have been exactly observed as reported by 2D techniques performed by Müller et al.[40] HRMS-ESI (m/z): [M+H]+ calcd for C4H14O3S2, 223.04571 Da; found 223.04626 Da.

Kinetics of 1,2-dithaine-1-oxide and 1,2-dithaine Cross-Linking

Figure 2A:
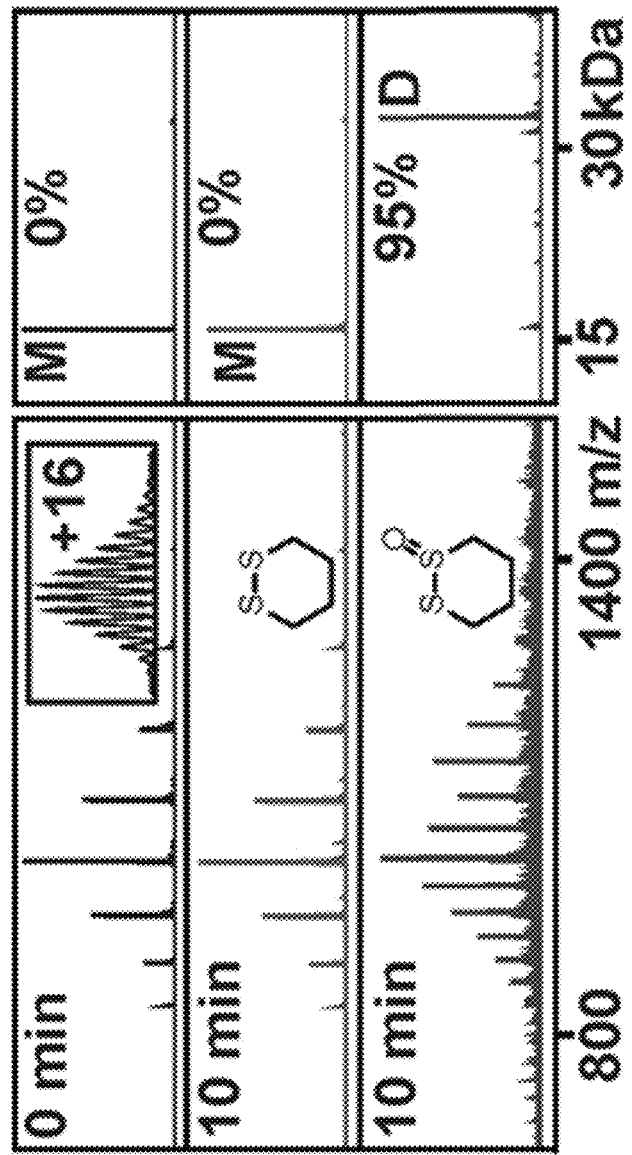
FIG. 2A. Thiol cross-linking by cyclic thiosulfinates kinetically stabilizes the SOD1 dimer in vitro and in cells. Representative raw (left) and deconvoluted (right) mass spectra. The 31,808 Da molecular mass of the cross-linked dimer (D) supports the mechanism proposed in FIG. 1A (e.g., two SOD1 monomers [2×15,844 Da (M)]+1,2-dithiane-1-oxide [136 Da]-oxygen [16 Da]).
Figure 2B:
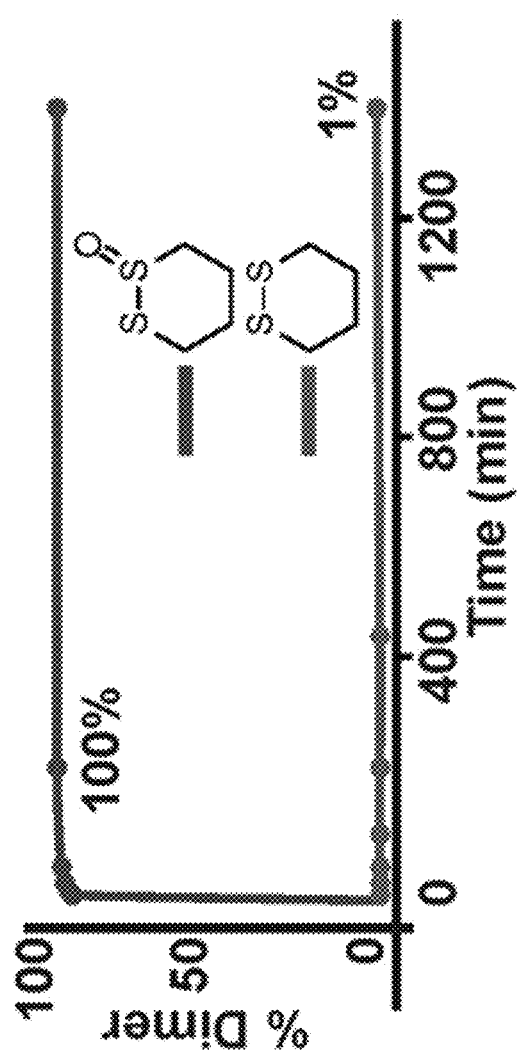
FIG. 2B. Representative data of FIG. 2A was used for calculating cross-linking rates. After 10 min of incubation 1,2-dithiane-1-oxide and 1,2-dithiane cross-linked 95% and 0% of SOD1, respectively.
Figure 2C:
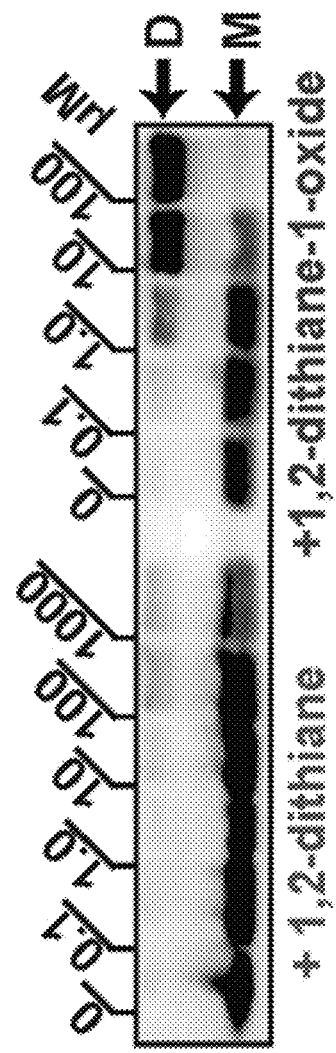
FIG. 2C. Consistent with the rate of cyclic disulfide cross-linkers being limited by thiol oxidation 1,2-dithiane cross-links only 11% of SOD1 after three days Western blot of SOD1 from HepG2 cells incubated with various concentrations of compounds for 30 min $EC_{50}$s for 1,2-dithiane-1-oxide cross-linking were 1-5 µM in HepG2 and HELA cells.
Figure 3:
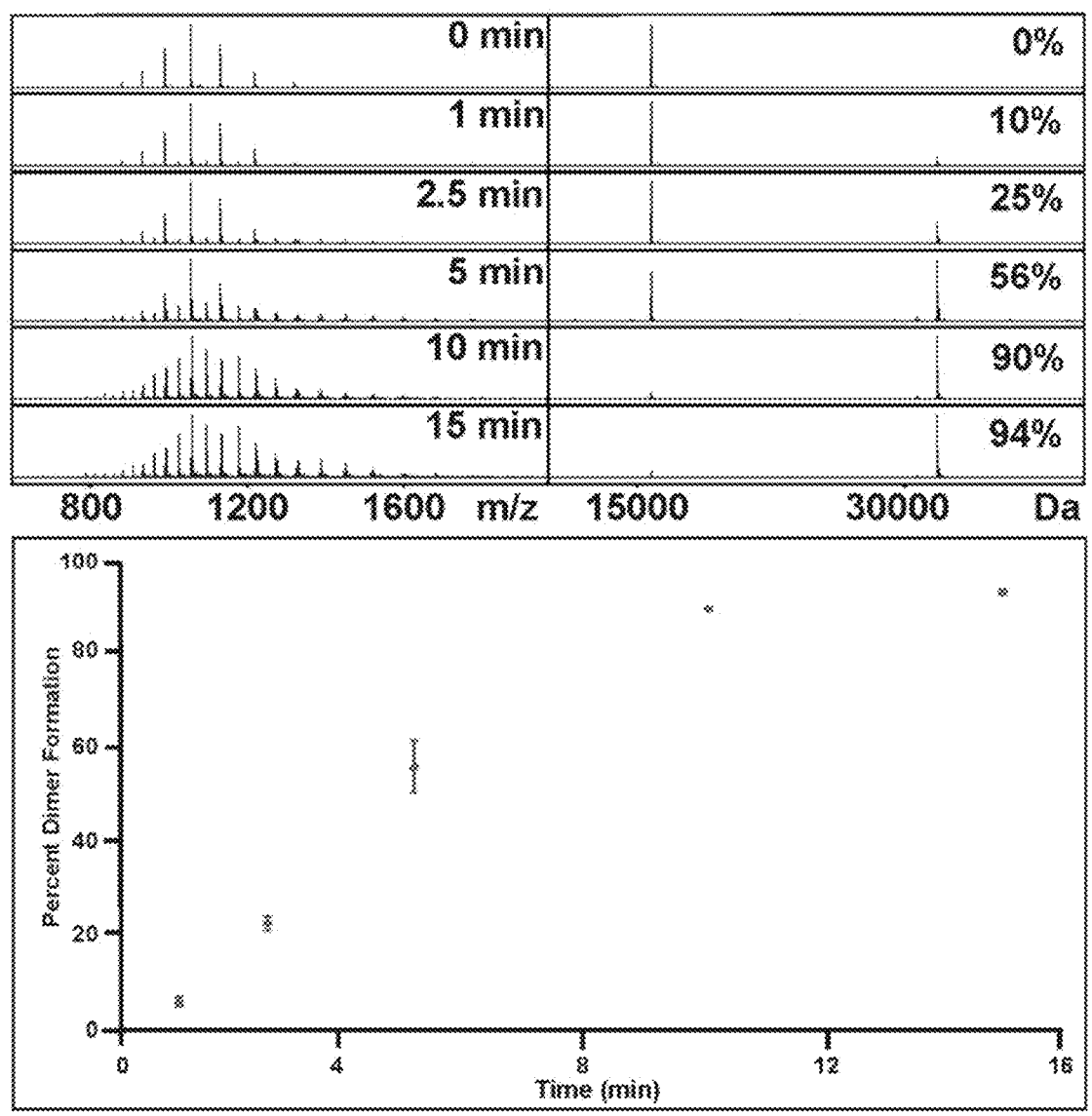
FIG. 3. Determination of 1,2-dithiane-1-oxide cross-linking half-life. A series of multi-concentration kinetics experiments was performed following the protocol of Singh et al.[13] and determined the overall second order rate constant of cyclic thiosulfinate-mediated cross-linking product formation to be $1.5 \times 10^4$ $M^{-1}$ $min^{-1}$ which, under the experimental conditions, extrapolates to a predicted half-life of 3 min for cross-linking SOD1 with 1,2-dithiane-1-oxide. Shown here are representative results from one concentration, 50 µM SOD1 with 20× excess 1,2-dithiane-1-oxide (1 mM).
Figure 4:
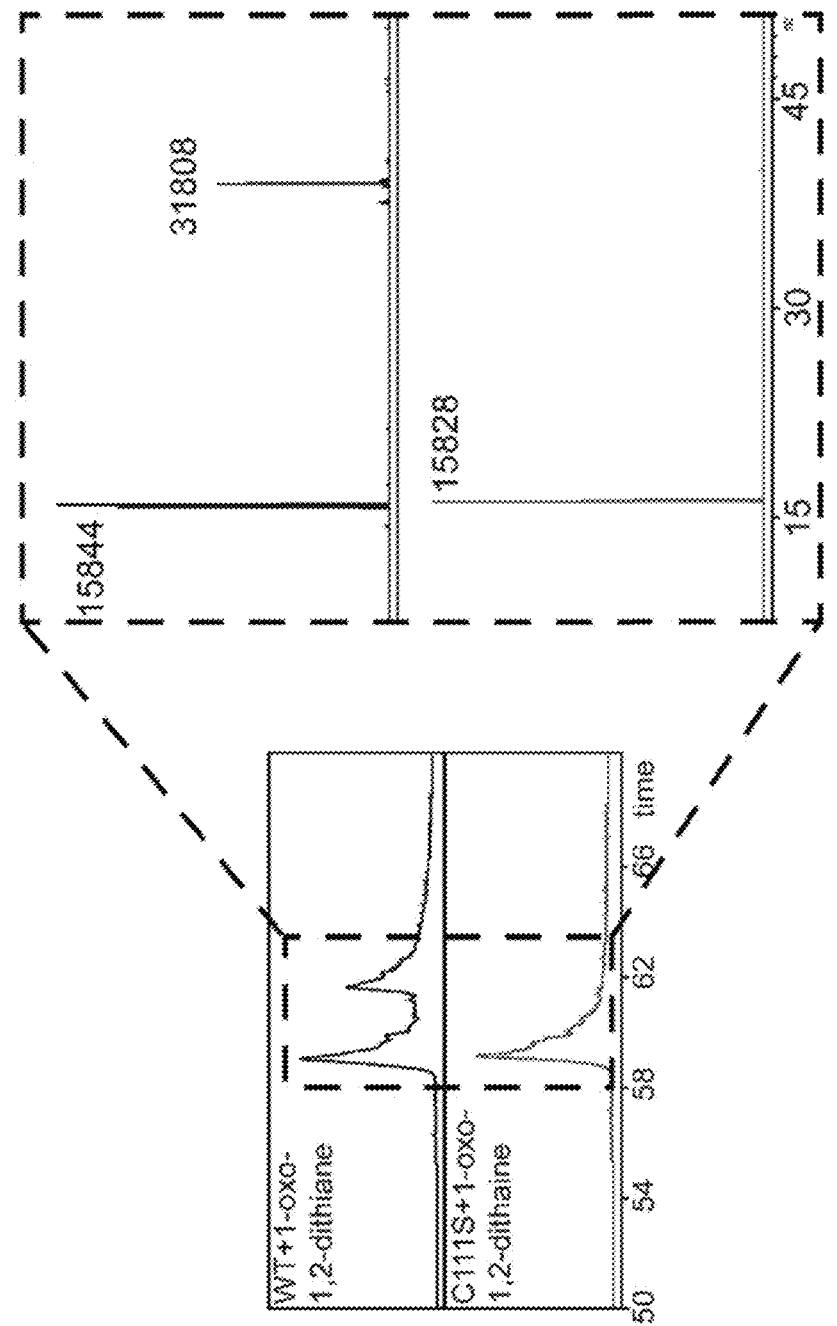
FIG. 4. Confirmation of 1,2-dithiane-1-oxide cross-linking site. LC-MS analysis of WT and $Cys_{111}$Ser SOD1 incubated with 1,2-dithiane-1-oxide. SOD1 variant $Cys_{111}$Ser shows no covalent dimer formation confirming the location of 1,2-dithiane-1-oxide cross-link at the $Cys_{111}$ pair at SOD1's dimer interface.
Figure 5:
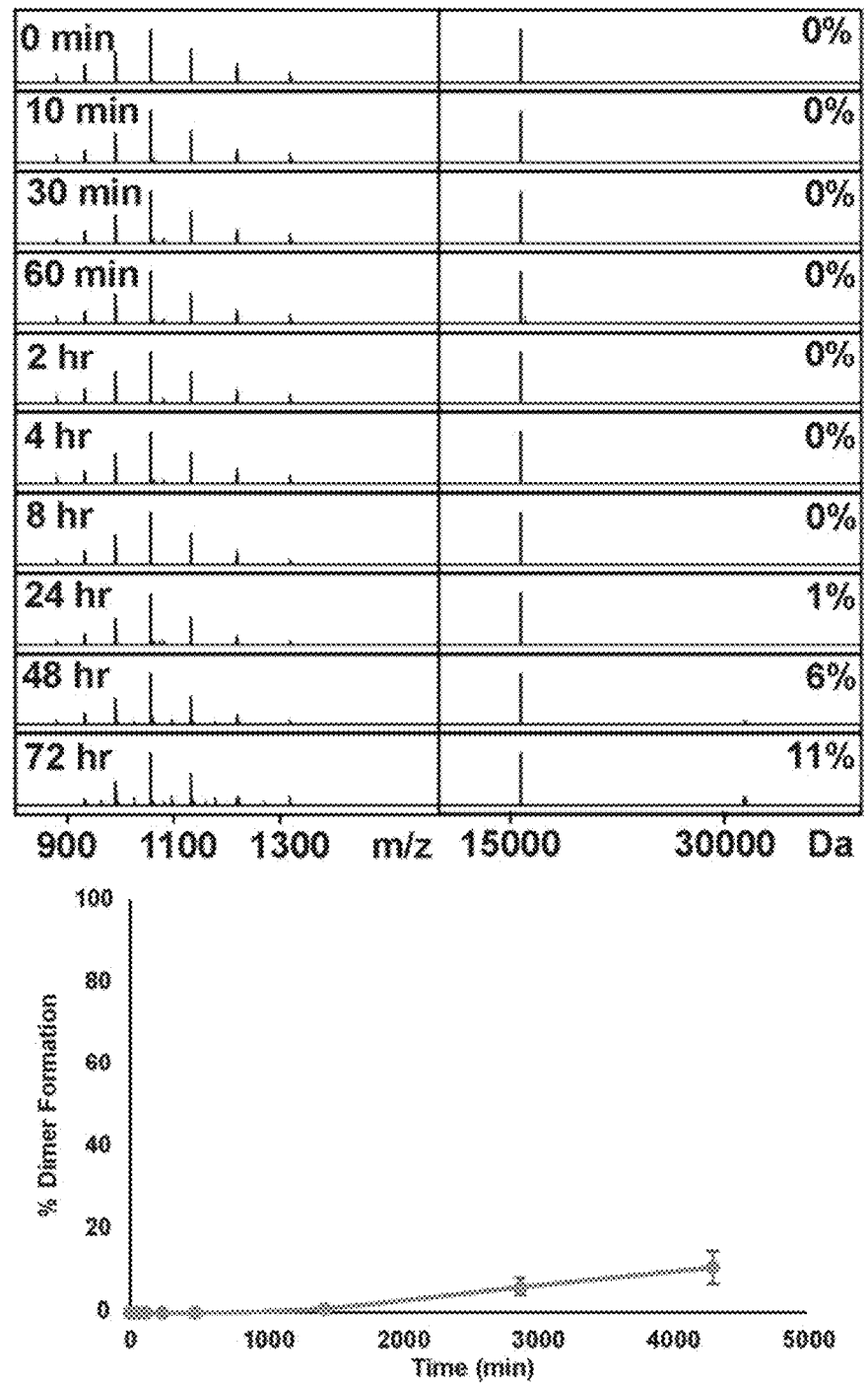
FIG. 5. Complete kinetics of 1,2-dithiane+SOD1 reaction. Incubation of 50 µM SOD1 with 20× excess 1,2-dithiane shows slow cross-link formation (compared to cyclic thiosulfinates) at the expected dimer mass of 31,808 Da, consistent with the mechanism proposed in FIG. 1A.
Figure 13:
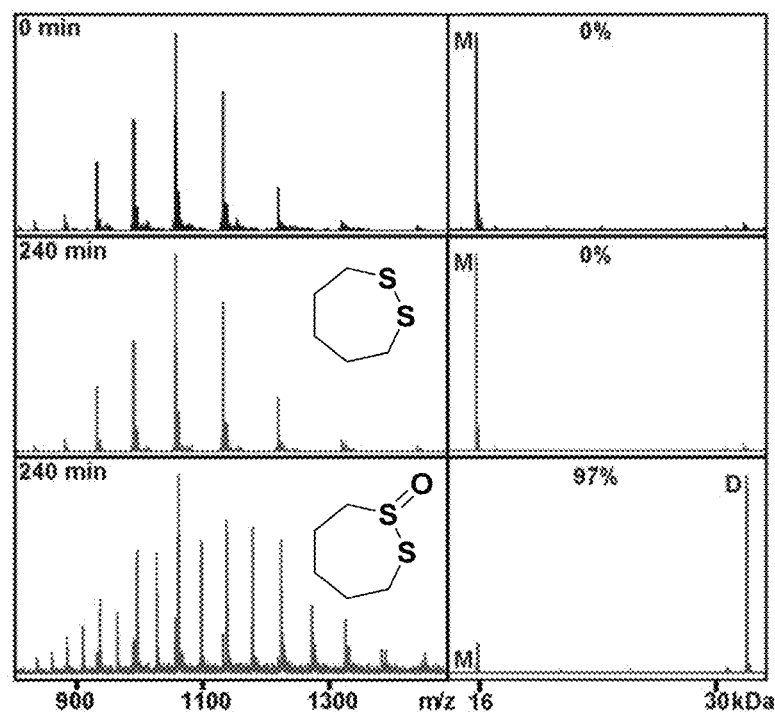
FIG. 13. Cross-linking SOD1 using 1,2-dithiepane-1-oxide. 1,2-dithiepane-1-oxide forms rapid and complete cross-link of SOD1 following the same proposed mechanism as 1,2-dithiane-1-oxide while 1,2-dithiepane does not. The observed covalent dimer (D) appeared at 31,824 Da (two SOD1 monomers [2×15,844 Da]+1,2-dithiepane-1-oxide [152 Da]-oxygen [16 Da]).
Figure 13:
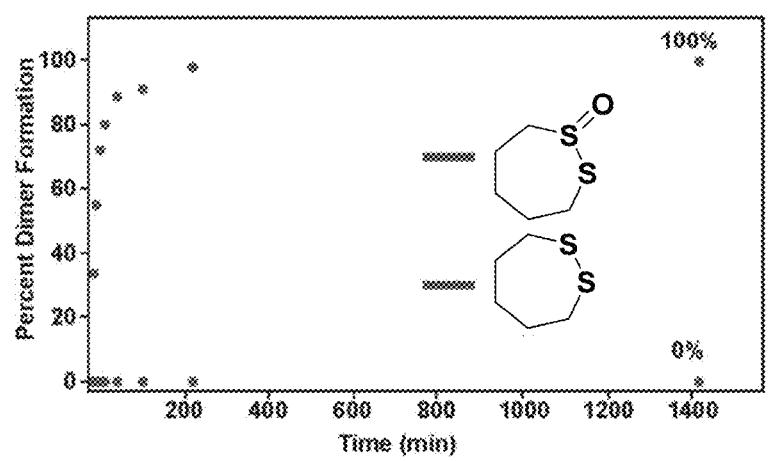
Figure 15:
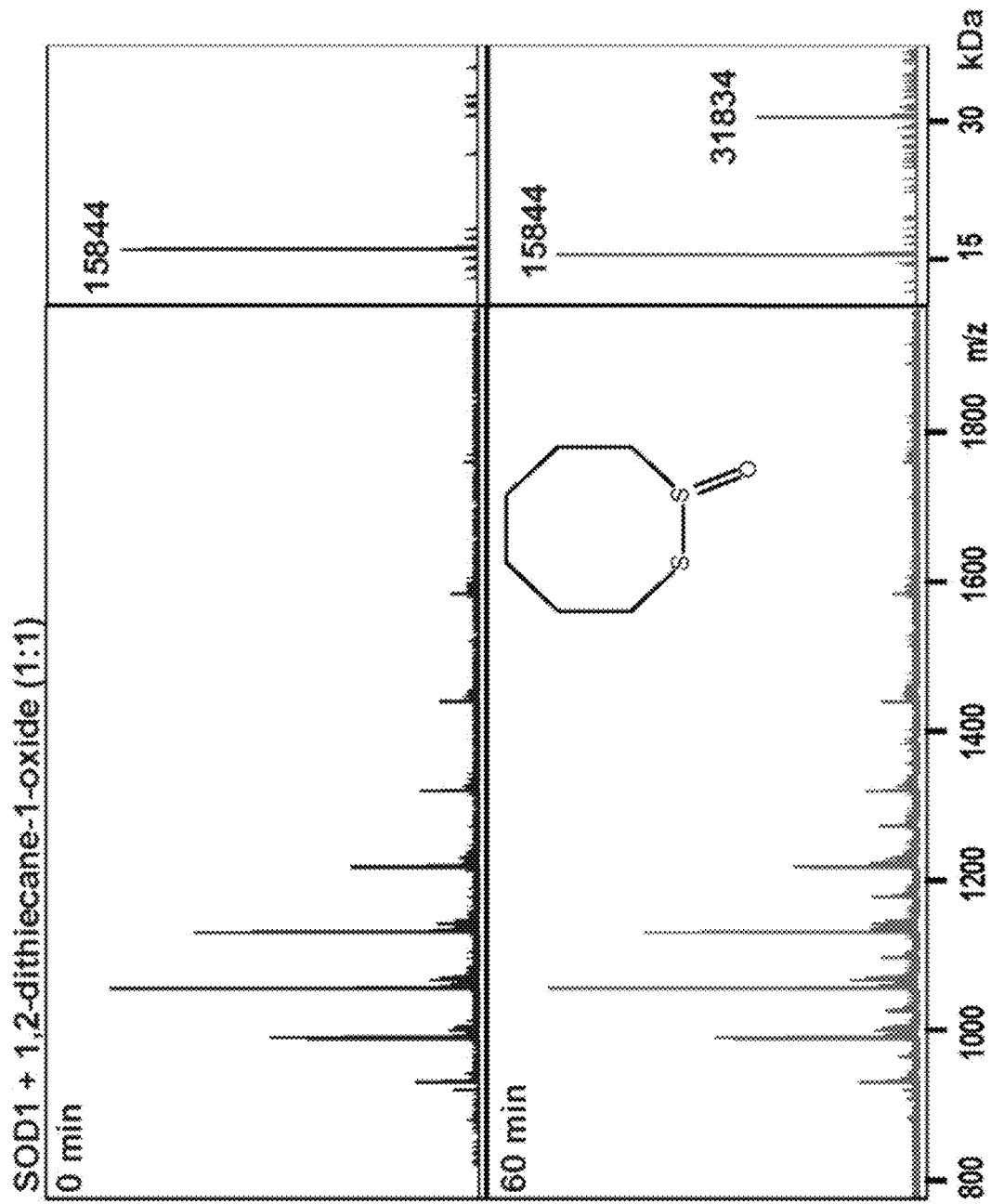
FIG. 15. Cross-linking SOD1 using 1,2-dithiocane-1-oxide. 1,2-dithiocane-1-oxide forms rapid and complete cross-link of SOD1 following the same proposed mechanism as 1,2-dithiane-1-oxide while 1,2-dithiocane does not. The observed covalent dimer (D) appeared at 31,834 Da (two SOD1 monomers [2×15,844 Da]+1,2-dithiocane-1-oxide [162 Da]-oxygen [16 Da]).

To test the cross-linking activity of cyclic disulfides and cyclic thiosulfinates, 1,2-dithiane and 1,2-dithiane-1-oxide were synthesized and incubated with SOD1, a homodimeric protein containing a solvent accessible thiol pair (Cys$_{111A+B}$, 8 Å apart) on adjacent subunits. The reaction was monitored using a mass spectrometry (MS) assay that uses a combination of increased voltage within the region of hypersonic gas expansion and brief treatment with 10% formic acid to create exclusively monomeric SOD1 or covalently cross-linked SOD1 dimer. Formic acid also quenches the reaction, transforming any reactive thiolates to unreactive thiols. As a result, if no reaction occurs, only apo SOD1 monomer is detected (FIG. 2, top). Consistent with our hypothesized mechanism: 1) 1,2-dithiane-1-oxide, but not 1,2-dithiane, resulted in rapid and complete dithiolate cross-linking (half-life ~2-3 min) of SOD1 (FIG. 2, middle and FIG. 3); 2) no binding to single Cys residues (SOD1 has free Cys$_{111}$ and Cys$_6$) was observed in any sample with either compound; 3) No cross-linking was observed without the loss of the oxygen from the S-oxo of 1,2-dithiane-1-oxide; 4) No cross-linking was observed when incubating 1,2-dithiane-1-oxide with C$_{111}$S SOD1 (FIG. 4). Given sufficient time for thiolates to be oxidized to sulfenic acid (which occurs on the order of days-weeks), even 1,2-dithiane was expected to cross-link SOD1. After 72 h of incubation with 1,2-dithiane, 11% of SOD1 had formed the expected covalent dimer (FIG. 5). Comparable results were observed from the incubation of SOD1 with 1,2-dithiepane and 1,2-dithiepane-1-oxide (FIG. 13). Comparable results were observed from the incubation of SOD1 with 1,2-dithiocane and 1-oxo-1,2-dithiocane (FIG. 15).

Kinetic studies of the cross-linking efficiency of 1,2-dithiane compared to 1,2-dithiane-1-oxide were performed in tandem. 50 μM human WT SOD1 in 10 mM ammonium acetate pH 7.4 was incubated with 1000 μM 1,2-dithiane or 1,2-dithiane-1-oxide (20× excess) at 37° C. Human WT SOD1 was expressed in yeast. Both 1,2-dithiane and 1,2-dithiane-1-oxide were dissolved in 100% HPLC grade methanol to a stock concentration of 25 mM. Dilution in HPLC-Grade water to 1 mM cyclic disulfide was performed prior to experimentation. As a negative control, 50 μM human WT SOD1 was incubated at 37° C. with 4% HPLC-grade methanol. At every time point, 1 μL of each sample was removed from their respective reaction vial for analysis. Samples were briefly (~30 seconds) incubated at room temperature with 10% formic acid to remove metals from SOD1 and quench cross-linking reaction prior to mass spectrometry analysis. Samples were then diluted to 1 μM SOD1 in 50:50 acetonitrile:water, 0.1% FA and analyzed by direct infusion into a Bruker SolariX XR FT-ICR mass spectrometer. The percent dimer formation was calculated by comparing the relative dimer (31,808 Da) and monomer (15,844 Da) MaxEnt deconvoluted peak heights (Dimer/(Dimer+Monomer)). Identical methods were used in the kinetics of α-lipoic acid and β-lipoic acid. Kinetics of 1,2-dithiepane vs. 1,2-dithiepane-1-oxide were performed at a 1:1 ratio of SOD1 dimer:cross-linker.

Expression and Purification of hSOD1 (WT and C111S)

Expression and purification of WT SOD1 and $C_{111}S$ SOD1 was carried out as previously published.[41-43] Briefly, human SOD1 cDNA cloned into the yeast expression vector YEp-351 was transformed into EGy118ΔSOD1 yeast and grown at 30° C. for 36-48 hours. Cultures were pelleted, lysed using 0.5 mm glass beads and a blender, and subjected to a 60% ammonium sulfate cut on ice. After ammonium sulfate precipitation, the sample was pelleted and the supernatant was diluted with ~0.19 volumes buffer (50 mM sodium phosphate, 150 mM sodium chloride, 0.1 M EDTA, 0.25 mM DTT, pH 7.0) to a final concentration of 2.0 M ammonium sulfate. The sample was then purified using a phenyl-Sepharose hydrophobic interaction chromatography column with a 300 mL linearly decreasing salt gradient from a high salt buffer (2.0 M ammonium sulfate, 50 mM sodium phosphate, 150 mM sodium chloride, 0.1 M EDTA, 0.25 mM DTT, pH 7.0) to a low salt buffer (50 mM sodium phosphate, 150 mM sodium chloride, 0.1 M EDTA, 0.25 mM DTT, pH 7.0). Samples containing SOD1 typically elute between 1.6-1.1 M ammonium sulfate, which was confirmed using gel electrophoresis. SOD1 containing fractions were pooled and exchanged to a 10 mM Tris (pH 8.0) buffer. The protein was then loaded onto a Mono Q 10/100 anion exchange chromatography column and eluted using a 200 mL linearly increasing salt gradient from a low salt buffer (10 mM Tris, pH 8.0) to a high salt buffer (10 mM Tris, pH 8.0, 1 M sodium chloride). The gradient is run from 0-30% 10 mM Tris, pH 8.0, 1 M sodium chloride and SOD1 eluted between 5-12% 10 mM Tris, pH 8.0, 1 M sodium chloride. SOD1 fractions from anion exchange were confirmed using gel electrophoresis. Final SOD1 containing fractions were pooled together, washed three times with 10 mM ammonium bicarbonate in a Millipore amicon centrifugal filter, and buffer exchanged into 10 mM ammonium acetate pH 7.4. Protein was stored at −80° C. until use.

Localization of Cross-Link Using Point Mutated C111S SOD1

1,2-Dithiane-1-oxide was initially dissolved in 100% DMSO. Recombinant human WT SOD1 and C111S SOD1 purified from yeast (10 μM) were incubated overnight at room temperature with 1,2-dithiane-1-oxide at 100 μM in 0.1% DMSO after dilution. Aliquots from each of the SOD1 incubations were individually diluted ten-fold with $H_2O$ containing 0.1% formic acid and analyzed using reversed phase C18 LC-MS on a Bruker HCT Ultra ion trap. The resulting data were processed using DataAnalysis 3.4 (Bruker Daltonics). Mass spectra were averaged across the retention times corresponding to when SOD1 eluted and were deconvoluted to determine the molecular weight of the uncharged species. Note, the acidic conditions employed during liquid chromatography and the relatively harsh electrospray ionization process resulted in loss of native metals and native dimer dissociation.

In Vitro Glutathione Competition Assay

Purified WT SOD1 was diluted to 10 μM in 10 mM ammonium acetate, pH 7.4. Protein was incubated with freshly prepared 100 μM 1,2-dithiane-1-oxide in 5% methanol and 1000 μM reduced glutathione (in water) at 37° C. for given time periods. Samples were extracted, briefly (10 s) with 10% formic acid to and analyzed at 0 min, 1 min, 10 min, 100 min, and 1000 mins Control samples included: 1) 10 μM SOD1 2) 10 μM SOD1+100 μM 1,2-dithiane-1-oxide 3) 10 μM SOD1+1000 μM reduced glutathione. Samples were briefly (30 seconds) incubated at room temperature with 10% formic acid to remove metals from SOD1 prior to mass spectrometry analysis. Samples were then diluted to 1 μM SOD1 in 50:50 acetonitrile:water, 0.1% FA and analyzed by direct infusion into a Bruker Solarix XR FT-ICR mass spectrometer. The percent dimer formation was calculated by comparing the relative dimer (31,808 Da) and monomer (15,844 Da) MaxEnt deconvoluted peak heights (Dimer/(Dimer+Monomer))

In Vitro DTT Competition Assay

Figure 6:
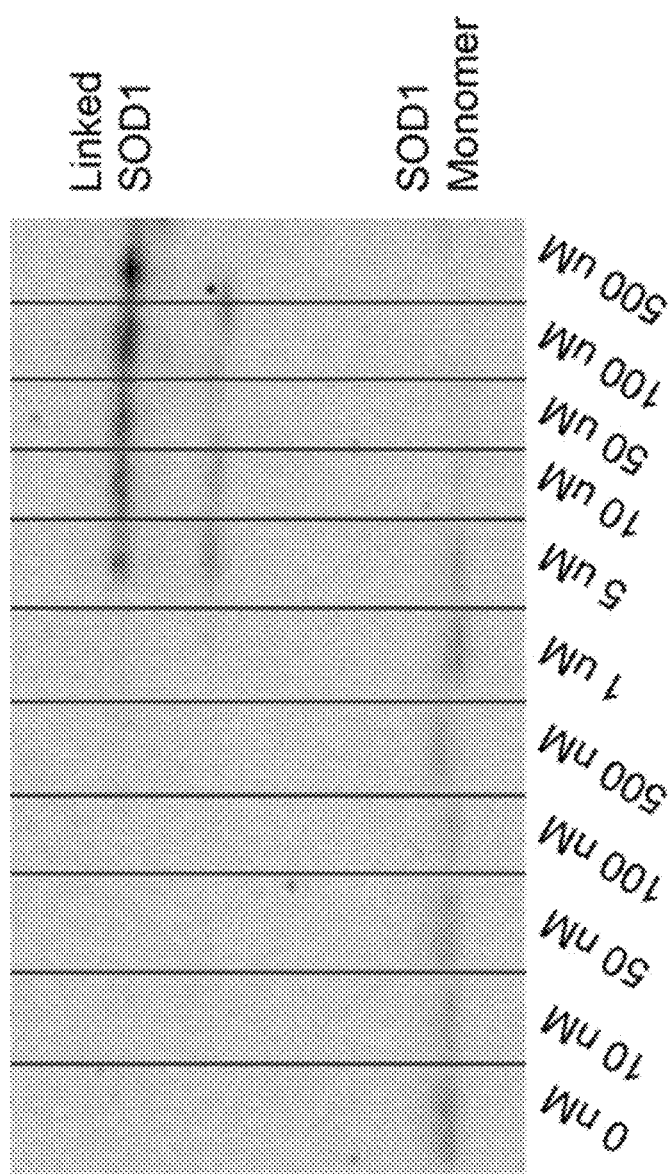
FIG. 6. 1,2-dithiane-1-oxide cross-links WT SOD1 in HeLa cells. Western blots of SOD1 extracted from HeLa cells treated with increasing concentrations of cyclic thiosulfinate 1,2-dithiane-1-oxide show an approximately 5 µM EC50 for 1,2-dithiane-1-oxide cross-linking of SOD1.
Figure 7:
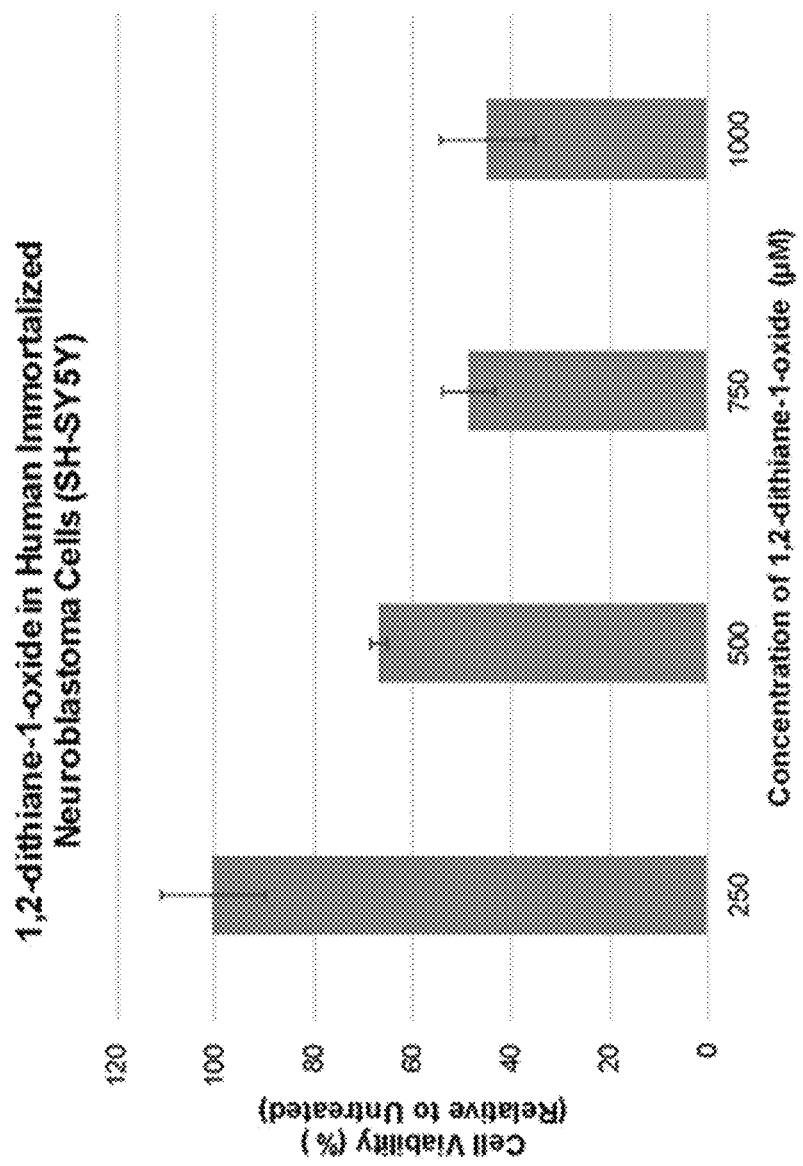
FIG. 7. 1,2-dithiane-1-oxide cell viability assay. SH-SY5Y cells incubated with various concentrations of 1,2-dithiane-1-oxide show cell viability is equivalent to untreated cells at cross-linker concentrations 50-fold higher than measured $EC_{50}$, and that the $LC_{50}$ is c.a. 200-fold that of the $EC_{50}$.
Figure 10A:
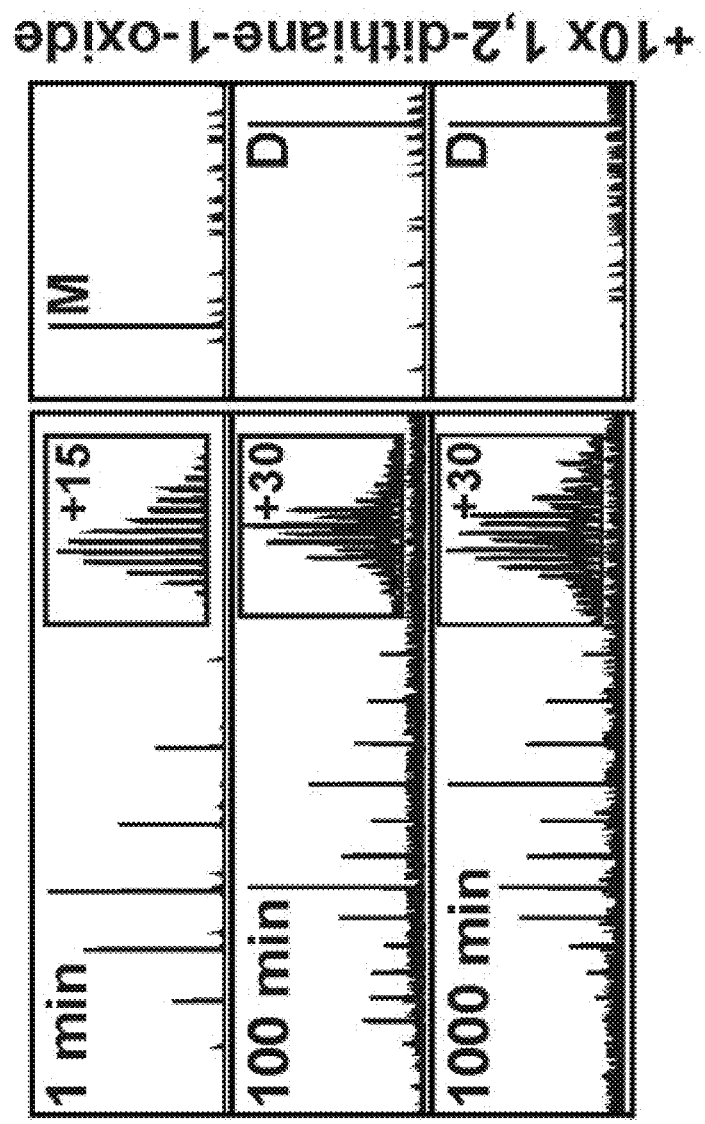
FIG. 10A. Cross-linking efficiency of 1,2-dithaine-1-oxide. Incubation of SOD1 with 10× 1,2-dithiane-1-oxide.
Figure 10B:
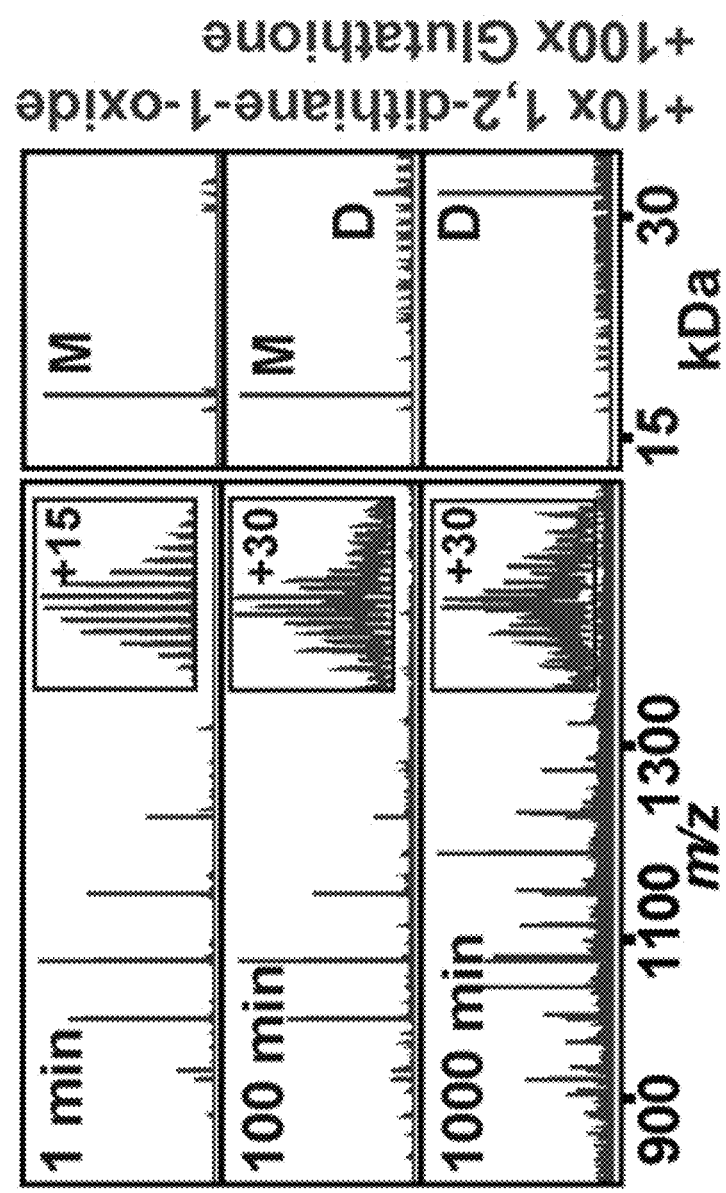
FIG. 10B. Cross-linking efficiency with 10× 1,2-dithiane-1-oxide and 100× reduced glutathione shows that even in the presence of excess glutathione, 1,2-dithiane-1-oxide can efficiently cross-link SOD1. In the presence of glutathione the rate of cross-linking was decreased, but the cross-linking yield (100%) was not affected.
Figure 11:
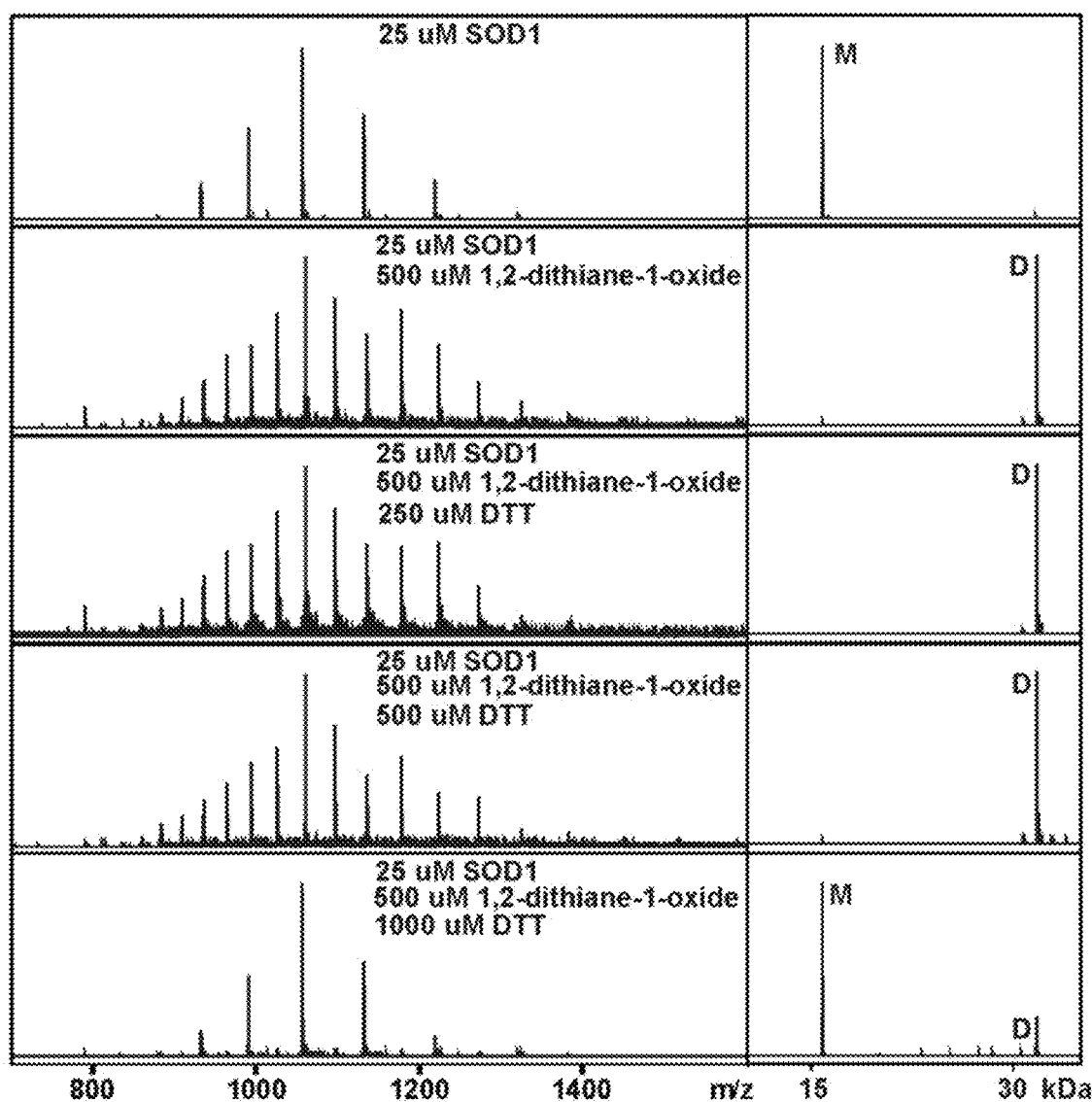
FIG. 11. Mass Spectrometric assay of 1,2-dithiane-1-oxide/DTT competition. SOD1 samples incubated for 24 h at various concentrations of DTT confirm 1,2-dithiane-1-oxide's ability to cross-link the thiol pair of SOD1 at 1:1=cross-linker:DTT.

Purified WT SOD1 was diluted to 50 μM in 10 mM ammonium acetate, pH 7.4. 2 μL of 50 μM SOD1 solution was incubated with 1 μL of 2 mM 1,2-dithiane-1-oxide and 1 μL of various concentrations of DTT. DTT solutions were made in 100% HPLC grade H2O. DTT solution concentrations were 1 mM, 2 mM and 4 mM. Samples were left to incubate at 37° C. for 24 h. Samples were then diluted to 1 μM SOD1 in 50:50 acetonitrile:water, 0.1% FA and analyzed by direct infusion into a Bruker Solarix XR FT-ICR mass spectrometer Cell Culture and 1,2-Dithiane-1-Oxide/1,2-Dithiane Dosing and α-Lipoic Acid/β-Lipoic Acid in Hep-G2 Cells To demonstrate the utility of 1,2-dithiane-1-oxide as a cell penetrating, dithiol pair cross-linker, the cross-linking reaction was examined both in two widely used human cell lines (Hep G2 and HeLa), and with purified SOD1 in the presence of competing reduced glutathione or DTT. Glutathione is present in human cells in concentrations up to 7 mM; Hep G2 and HeLa cells both contain approximately 5 mM glutathione.[30] Hep G2 cells (FIG. 2, bottom) and HeLa cells (FIG. 6) incubated with various concentrations of 1,2-dithaine-1-oxide for 30 min showed an $EC_{50}$ of ~5 μM in western blots, confirming that cellular conditions do not prohibit cross-linking. Cell viability was not affected by 1,2-dithiane-1-oxide concentrations that were 50-fold higher than the $EC_{50}$, and the $LC_{50}$ of 1,2-dithiane-1-oxide was approximately 200-fold greater than its $EC_{50}$ (FIG. 7). Consistent with the cellular studies, cross-linking of purified SOD proceeded to completion in the presence of 10:1 ratio of glutathione:1,2-dithiane-1-oxide (FIG. 10), and even in the presence of equimolar concentrations of the reducing agent dithiothreitol (DTT) (FIG. 11). The rate of cross-linking was decreased in the presence of competing reductants, presumably due to reversible thiolate-disulfide interchange between reductants and 1,2-dithiane-1-oxide (no glutathionyl or DTT adducts with 1,2-dithiane-1-oxide or SOD1 were observed). These results confirm the utility of these cross-linkers even in presence of modest amounts of additional reducing agents.

Figure 8:
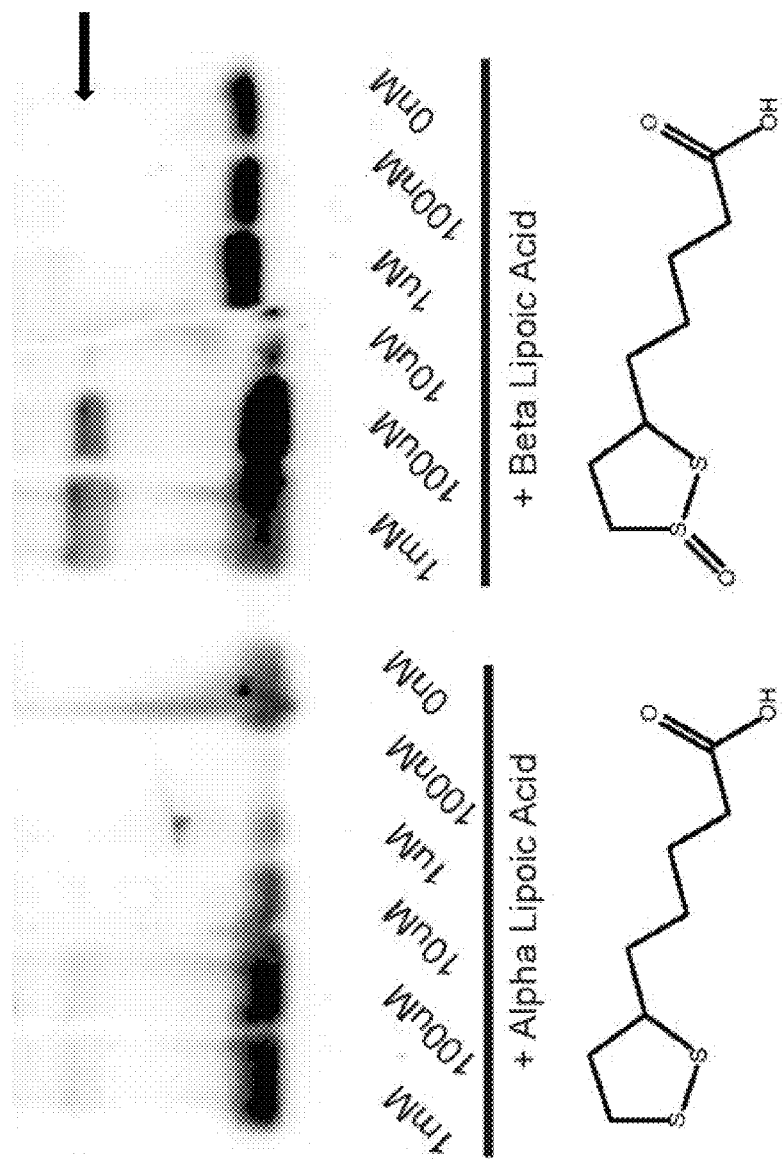
FIG. 8. The cyclic thiosulfinate, β-lipoic acid cross-links SOD1 in Hep G2 cells, and does so more efficiently than the cyclic disulfide, α-lipoic acid. Western blots of SOD1 extracted from Hep G2 treated with increasing concentrations of lipoic acids (α and β) shows the 1-oxide form increases in vivo cross-linking (as measured by formation of the SOD1 dimer, arrow, following denaturing SDS-PAGE).
Figure 9:
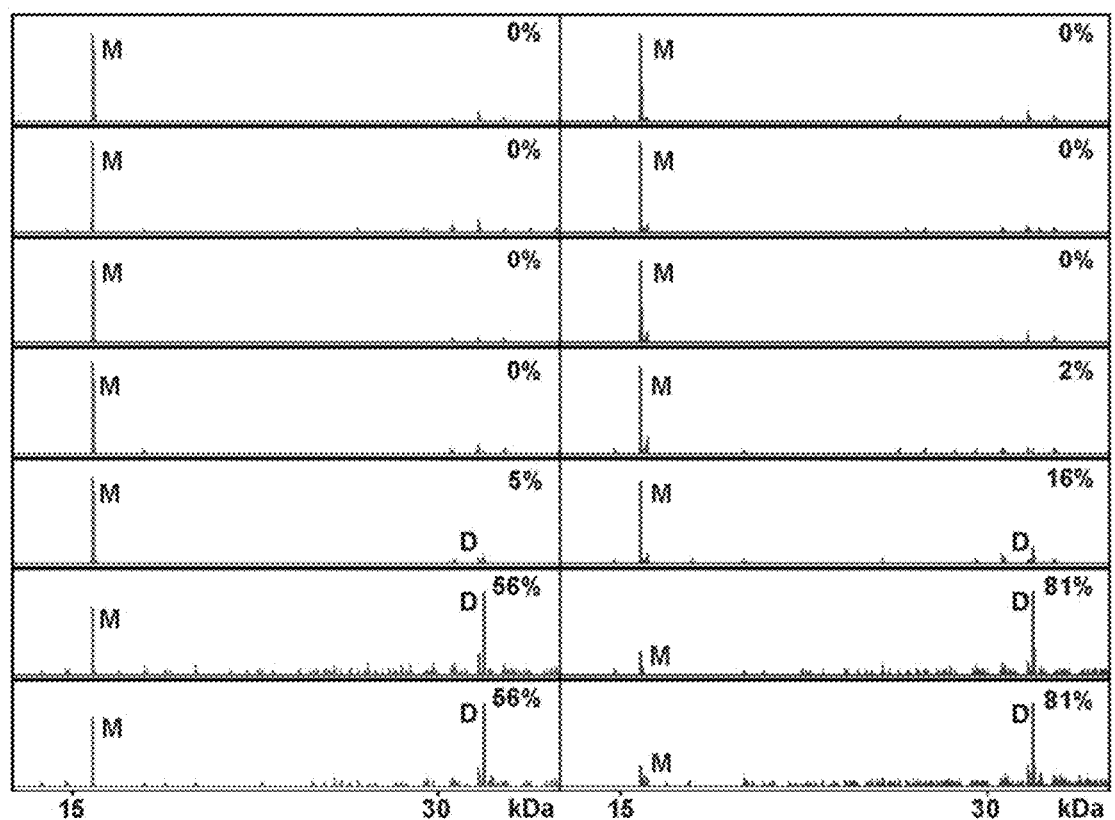
FIG. 9. Mass spectrometry assay of α-lipoic acid vs. β-lipoic acid cross-linking of SOD1. Both rate and extent of covalent cross-linking of SOD1 is increased by oxidation of α-lipoic acid to β-lipoic acid.
Figure 9:
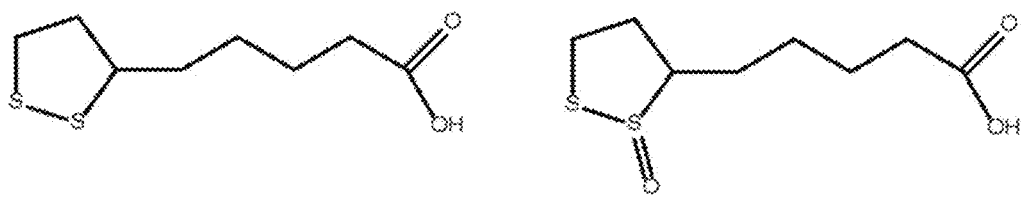

Cyclic disulfides[31] and their derivatives (e.g., dithiolene thiones)[24] have been used therapeutically and many of their targets are known. However, the binding mechanism of these drugs, including that of the nutritional supplement and diabetic complication treatment, α-lipoic acid (ALA), have not been characterized.[25] To broaden the applicability of cyclic disulfide mediated cross-linking and explore a potential mode of action, ALA was purchased and β-lipoic acid (BLA), which was observed in mass spectrometry assays of ALA nutritional supplements, was synthesized and assayed as above. Compared to ALA, BLA cross-linked SOD1 in cells and cross-linked 30% more SOD1 in vitro (FIG. 8 and FIG. 9). Notably, the terminal carboxylic acid on ALA and BLA presents an opportunity for functionalization.[32]

Hep G2 cells were cultures in DMEM with 10% fetal bovine serum and penicillin/streptomycin in 96 well Costar® Corning CellBIND plate with 5% $CO_2$ at 37° C. The cells were cultured to monolayer confluency. 20 mM, 2 mM, 200 μM, 20 μM, and 2 μM stocks of 1,2-dithiane and 1,2-dithiane-1-oxide were prepared in 100% DMSO. Stocks were diluted twenty-fold in 1×PBS (final DMSO 5%). Cells were treated with 200 uL of compound and incubated for 30 minutes at 37° C. 5% $CO_2$. Cells were washed with 1×PBS and 20 μL of 6× nonreducing sample buffer was added to each well. The 96 well plate was heated to 90° C. for 10 minutes. Samplers were spun at 14000 RPM for 5 minutes in a Beckman Coulter Microfuge®18 centrifuge. Samples were run using a Bio Rad Mini-Protean electrophoresis chamber on 12% precast TGX polyacrylamide gels at 150V. After separation was complete, gels were extracted from the cassettes and incubated in an in-house transfer buffer for 10 minutes are 90° C. to ensure thorough transfer of protein bands and thorough binding of antibody (25 mM Tris, 192 mM glycine, 10 mM 2-mercaptoethanol, 0.1% SDS). Transfer was performed with a Bio Rad Trans-blot turbo transfer system using a trans-clot turbo transfer pack. Membranes were dried, blocked with 5% milk for 2 h at room temperature. Membranes were then probed with primary antibody, anti-SOD1 antibody SOD100 overnight at 4° C. Membranes are incubated with HRP-labeled secondary antibodies and visualized using ECL Western Blotting Substrate and imaged using the ChemiDoc MP.

Cell Culture and 1,2-Dithaine-1-Oxide Dosing Assay in HeLa Cells

HeLa cells were cultured in DMEM with 10% fetal bovine serum and penicillin/streptomycin in 24 well Costar® Corning CellBIND plate with 5% $CO_2$ at 37° C. The cells were cultured to monolayer confluency. A 100 mM concentration of 1,2-dithiane-1-oxide was made by dissolving in DMSO. The 100 mM solution diluted to various concentrations with 1×PBS solution. 1 mL of solutions was added to the HeLa cells in the 24 well plate. 1,2-Dithiane-1-oxide was allowed to interact with the cells for 1 h. Cells were washed 2× with 1 mL PBS. After removing the second PBS wash, the cells were then treated with 6× non-reducing SDS sample buffer and collected. The collected cell lysate was divided into two parts. One half was treated with 5% β-ME, to remove bound cyclic disulfides, as negative controls. The other half was treated with equal amount of milliQ water. All the cell lysate samples were then heated at 80° C. for 10 minutes in an Eppendorf Thermomixer. The samples were spun at 14000 rpm for 5 minutes in Beckman Coulter Microfuge centrifuge. HeLa cell extracts were separated on 12% SDS-polyacrylamide TrisHCl gels run at 80 V at room temperature. Proteins were transferred to nitrocellulose membranes for Western blotting. Monomer and covalently-linked dimer SOD1 were detected using the rabbit polyclonal anti-SOD1 antibody SOD100. Membranes are incubated with HRP-labeled secondary antibodies and visualized using ECL Western Blotting Substrate and imaged using the ChemiDoc MP.

Cell Culture and 1,2-Dithiane-1-Oxide Cell Viability Assay

Human immortalized neuroblastoma cells (SH-SY5Y) were purchased from ATCC (Manassas, Virginia, USA). Cells were grown in Eagle's Minimum Essential Medium (EMEM) supplemented with 10% fetal bovine serum at 37° C. and 5% $CO_2$ to >70% confluency. Cells were treated with 200 μL of various concentrations of 1,2-dithiane-1-oxide in 2% DMSO (250 μM, 500 μM, 750 μM, and 1000 μM) and allowed to incubate for 24 h in a 96 well plate (Corning Inc., Corning, New York, USA). Following incubation with 1,2-dithaine-1-oxide, 22 μL of PrestoBlue® was added to each well and allowed to incubate for 10 min at 37° C. Excitation/emission was measured at 560/590 (in nm) using an Infinite® 200 plate reader (Tecan, Mannedorf, Switzerland). Cell viability was quantified relative to untreated cells.

Computational Methods

All computations were carried out with Gaussian 09, Rev E.01.[44] The reported stationary points were optimized using the M06-2X[45] density functional at the DFT level of theory. The Gaussian 09 default ultrafine integration grid and the polarizable continuum model (PCM) using the integral equation formalism variant (IEF-PCM)[46-48] using parameters for water were utilized. Each stationary point was subjected to a vibrational analysis and all transition structures have exactly one negative frequency, while all other stationary points have all frequencies greater than 0 indicating local minima A single point energy calculation was then performed on the 6-31+G(d,p)-optimized geometries at the DFT level of theory with ultrafine grid and PCM model as mentioned earlier. Single point energy were performed using the with 6-311+G(d,p) basis set. The total energy was calculated by adding the free energy correction and the single point energy.

The parameters for the transition structure conformational search were identical for the minima, but the forming S—S bond was constrained at 2.4 Angstroms for the cyclic disulfide ring opening step (TS5→2a and TS1→2b) and 2.3 Angstroms for the thiolate/sulfenic acid condensation reaction (TS(3a,b→4)). Each constrained transition state search produced 10 structures within 12 kcal/mol (according to OPLS2005) which were subjected to a transition state search. The reported structures in FIG. 1 are the lowest energy transition structures for each transformation.

QM Calculations are Consistent with Empirical Studies

Using transition state theory (Eyring equation) rates were extrapolated from the calculated transition states (TS (1→2b) and TS(5→2a)), and found these were consistent with the myriad of published small molecule and protein experimental data (see below), and the data presented here. In particular, the QM results provide mechanistic insight into how decreasing the pKa of the leaving group sulfur (via sulfenic acid anion instead of a sulfur anion) increased the overall reaction rate by two separate mechanisms (i.e., in addition to eliminating the rate determining thiol oxidation, cyclic thiosulfinates decrease the barrier of the new rate limiting step, thiolate-disulfide interchange). Specifically, a series of detailed (multi-concentration) kinetics experiments was performed following the protocol of Singh et al. and determined the overall second order rate constant of cyclic thiosulfinate-mediated cross-linking product formation to be 1.5×104 M-1 min-1 which, under our experimental conditions, extrapolates to a predicted half-life of 2.7 min for cross-linking SOD1 with 1,2-dithiane-1-oxide.[49] Notably this value is consistent with half-life fitted from FIG. 1 (2.2 min) and is consistent with the absolute rate extrapolated from the calculated value of 13.1 kcal/mol for the thiol-disulfide intermediate 2b. being the rate determining step. The thiol-disulfide exchange reaction of oxidized DTT (cyclic disulfide) and reduced glutathione, which provides the closest analogy to the 1,2-dithiane data presented here, has an extrapolated half-life of >200 mins (rate constant of 1.8×102 M-1 min-1).[50] In fact, the rates observed and calculated for cyclic thiosulfinates were faster than any ever reported for cyclic disulfides (to our knowledge, the fastest reported rate of thiol-disulfide interchange is the reaction of Papain-S—SCH3 with DTT which gives a rate constant of 3.3×103 M-1 min-1 and an extrapolated half-life of 12 min).[51] These combined results demonstrate that thiosulfinates speed the overall rate both by eliminating the rate determining-S oxidation, and then by decreasing the new rate limiting step, thiolate-disulfide interchange. It was noted that although the reported condensation reaction rates of thiolates and sulfenic acids vary considerably, our experimentally determined rate constants are near the median of reported values, and are also consistent with the 11.0 kcal/mol transition state (TS(3a,3b→4)) reported in as-reviewed FIG. 1. For example, Gupta et al. reported the rate constants of disulfide formation through sulfenic acid/thiolate condensation range from >106 M-1 min-1 (Cys-SOH+Cys) to 1.3×103 M-1 min-1 (HSA-SOH+Cys), which extrapolate to half-lives ranging from milliseconds to 30 mins, respectively, under our experimental conditions.[52]

Thapa et al. highlighted the difficulty of computing pKa's of thiols without explicit solvation, and experimental rates of thiol-disulfide exchange generally decrease by three orders of magnitude in protic compared to aprotic solvents, and by as much as nine orders of magnitude in water compared to the gas phase.[53-54] Given these obstacles, and that the protein includes both protic and aprotic environments, continuum model-based calculations for intermediates 3a and 3b were not reported. The experimental data required to estimate the pKa of this intermediate was not obtained, which is therefore listed as the arbitrary value of 0 kcal/mol.[55] Note, however, this value is consistent with the experimentally determined rates, which imply that the energy of intermediate 3a,3b cannot be higher than c.a. 3 kcal/mol, as well as the lack of observation of mono-thiol intermediates, which implies that its energy probably isn't lower than c.a. −3 kcal/mol.

Use of Cyclic Thiosulfinates for Nanoparticle, Dendrimer, and Polymer Syntheses

Figure 14:
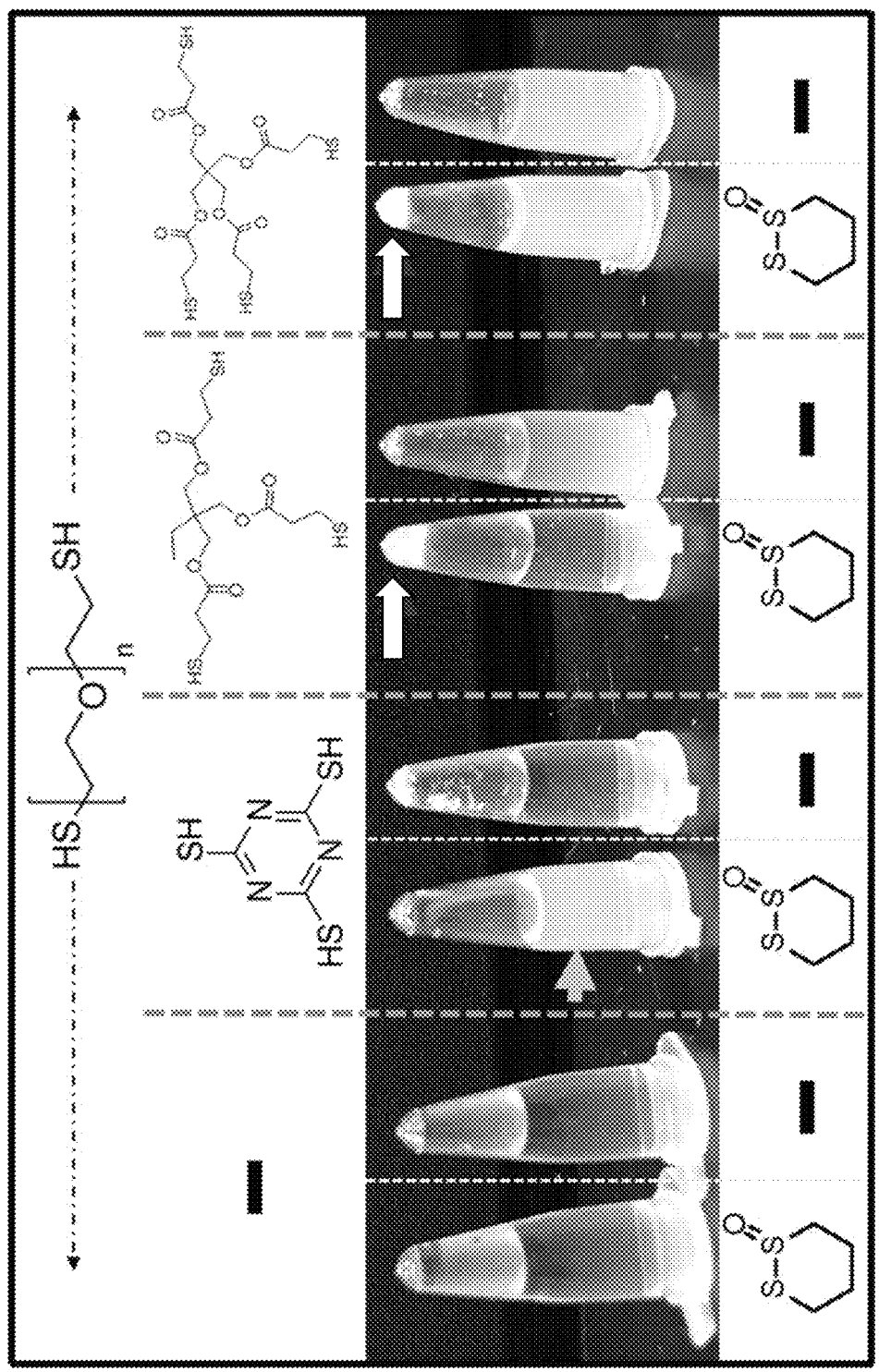
FIG. 14. Cyclic thiosulfinate-mediated polymerization. All mixtures contained polyethylene dithiol. From left to right mixtures contained no facilitator (−), Trithiocyanuric acid, Trimethylolpropane Tris(3-MP), and Pentaerythritol tetra(3-MP) and either 1,2-dithiane-1-oxo cross-linker or no cross-linker (−). Arrows to solid mass indicate polymer; arrow to mixture indicates putative nanoparticles. MP=3-mercaptopropionate.

It was demonstrated that cyclic thiosulfinates could replace diene (e.g., bismaleimides) cross-linkers for nanoparticle, dendrimer, and polymer syntheses and the results are shown in FIG. 14.

Briefly, polyethylene dithiol was mixed with either: no facilitator (−); trithiocyanuric acid; trimethylolpropane tris (3-mercaptopropionate); or pentaerythritol tetra(3-mercaptopropionate) and each mixture was treated with either 1,2-dithiane-1-oxo cross-linker or no cross-linker (−). The red arrows in FIG. 14 indicate a reaction in which polymer formed and the orange arrow indicate a reaction in which putative nanoparticles formed. Poly(ethylene glycol) dithiol (PEG-DT, e.g., with average $M_n$ of 1,500) was mixed with 1,2-dithiane-1-oxo cross-linker to undergo a solid state reaction to produce a transparent polymer.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the claims.

REFERENCES CITED (1) Kolb, H. C.; Finn, M. G.; Sharpless, K. B., *Angew. Chem., Int. Ed.* 2001, 40 (11), 2004-2021.
(2) Kuhl, N.; Geitner, R.; Vitz, J.; Bode, S.; Schmitt, M.; Popp, J.; Schubert, U. S.; Hager, M. D., *J. Appl. Polym. Sci.* 2017, 134 (19), 1-8.
(3) Lockhart, J. N.; Beezer, D. B.; Stevens, D. M.; Spears, B. R.; Harth, E., *J. Control. Release* 2016, 244, 366-374.
(4) Hoyle, C. E.; Bowman, C. N., *Angew. Chem., Int. Ed.* 2010, 49 (9), 1540-1573.
(5) Wang, J. Q.; Zhang, F. J.; Tsang, W. P.; Wan, C.; Wu, C., *Biomaterials* 2017, 120, 11-21.
(6) Killops, K. L.; Campos, L. M.; Hawker, C. J., *J. Am. Chem. Soc.* 2008, 130 (15), 5062-5064.
(7) Marculescu, C.; Kossen, H.; Morgan, R. E.; Mayer, P.; Fletcher, S. A.; Tolner, B.; Chester, K. A.; Jones, L. H.; Baker, J. R., *Chem. Commun.* 2014, 50 (54), 7139-7142.
(8) Auclair, J. R.; Boggio, K. J.; Petsko, G. A.; Ringe, D.; Agar, J. N., *Proc. Natl. Acad. Sci. U.S.A.* 2010, 107 (50), 21394-21399.
(9) Konermann, L.; Vahidi, S.; Sowole, M. A., *Anal. Chem.* 2014, 86 (1), 213-232.
(10) Baillie, T. A., *Angew. Chem., Int. Ed.* 2016, 55 (43), 13408-13421.
(11) Valenzano, K. J.; Khanna, R; Powe, A. C.; Boyd, R.; Lee, G.; Flanagan, J. J.; Benjamin, E. R., *Assay Drug Dev. Technol.* 2011, 9 (3), 213-235.
(12) Narita, A.; Shirai, K.; Itamura, S.; Matsuda, A.; Ishihara, A.; Matsushita, K.; Fukuda, C.; Kubota, N.; Takayama, R.; Shigematsu, H.; Hayashi, A.; Kumada, T.; Yuge, K.; Watanabe, Y.; Kosugi, S.; Nishida, H.; Kimura, Y.; Endo, Y.; Higaki, K.; Nanba, E.; Nishimura, Y.; Tamasaki, A.; Togawa, M.; Saito, Y.; Maegaki, Y.; Ohno, K.; Suzuki, Y., *Ann. Clin. Transl. Neurol.* 2016, 3 (3), 200-215.
(13) Liu, Q.; Sabnis, Y.; Zhao, Z.; Zhang, T.; Buhrlage, S. J.; Jones, L. H.; Gray, N. S., *Chem. Biol.* 2013, 20 (2), 146-159.
(14) Nelson, V.; Ziehr, J.; Agulnik, M.; Johnson, M., *Onco Targets Ther.* 2013, 6, 135-143.
(15) Hald, J.; Jacobsen, E., *Lancet (London, England)* 1948, 2 (6539), 1001-1004.
(16) Lindberg, P.; Nordberg, P.; Alminger, T.; Brandstrom, A.; Wallmark, B., *J. Med. Chem.* 1986, 29 (8), 1327-1329.
(17) Shin, J. M.; Besancon, M.; Simon, A.; Sachs, G., *Biochim. Biophys. Acta* 1993, 1148 (2), 223-233.
(18) Ferri, N.; Corsini, A.; Bellosta, S., *Drugs* 2013, 73 (15), 1681-1709.
(19) Burns, J. A.; Whitesides, G. M., *J. Am. Chem. Soc.* 1990, 112 (17), 6296-6303.
(20) Szajewski, R. P.; Whitesides, G. M., *J. Am. Chem. Soc.* 1980, 102 (6), 2011-2026.
(21) Singh, R.; Whitesides, G. M., *J. Am. Chem. Soc.* 1990, 112 (17), 6304-6309.
(22) Abegg, D.; Gasparini, G.; Hoch, D. G.; Shuster, A.; Bartolami, E.; Matile, S., *J. Am. Chem. Soc.* 2017, 139 (1), 231-238.
(23) Barcan, G. A.; Zhang, X. Y.; Waymouth, R. M., Structurally Dynamic Hydrogels Derived from 1,2-Dithiolanes. *J Am Chem Soc* 2015, 137 (17), 5650-5653.
(24) Nare, B.; Smith, J. M.; Prichard, R. K., *Biochem. Pharmacol.* 1992, 43 (6), 1345-1351.
(25) Shay, K. P.; Moreau, R. F.; Smith, E. J.; Smith, A. R.; Hagen, T. M., *Biochim. Biophys. Acta* 2009, 1790 (10), 1149-1160.
(26) Fang, J.; Ye, S. H.; Wang, J.; Zhao, T.; Mo, X. M.; Wagner, W. R., *Biomacromolecules* 2015, 16 (5), 1622-1633.
(27) Zong, L.; Bartolami, E.; Abegg, D.; Adibekian, A.; Sakai, N.; Matile, S., *ACS Cent. Sci.* 2017, 3 (5), 449-453.
(28) Gupta, V.; Carroll, K. S., *Chem. Sci.* 2016, 7 (1), 400-415.
(29) Shaked, Z.; Szajewski, R. P.; Whitesides, G. M., *Biochemistry* 1980, 19 (18), 4156-4166.

(30) Jiang, X.; Yu, Y.; Chen, J.; Zhao, M.; Chen, H.; Song, X.; Matzuk, A. J.; Carroll, S. L.; Tan, X.; Sizovs, A.; Cheng, N.; Wang, M. C.; Wang, J., *ACS Chem. Biol.* 2015, 10 (3), 864-874.

(31) Sun, H.; Yao, W.; Tang, Y.; Zhuang, W.; Wu, D.; Huang, S.; Sheng, H., *J. Clin. Lab. Anal.* 2017, 31 (6), 1-7.

(32) Gasparini, G.; Sargsyan, G.; Bang, E. K.; Sakai, N.; Matile, S., *Angew. Chem., Int. Ed.* 2015, 54 (25), 7328-7331.

(33) Schmidt, A.-C.; Koppelt, J.; Neustadt, M.; Otto, M., *Rapid Commun. Mass Spectrom.* 2007, 21 (2), 153-163.

(34) Alon, A.; Grossman, I.; Gat, Y.; Kodali, V. K.; DiMaio, F.; Mehlman, T.; Haran, G.; Baker, D.; Thorpe, C.; Fass, D., *Nature* 2012, 488 (7411), 414-418.

(35) Owen, G. R.; Channell, J. A.; Forsyth, V. T.; Haertlein, M.; Mitchell, E. P.; Capovilla, A.; Papathanasopoulos, M.; Cerutti, N. M., *Biochemistry* 2016, 55 (15), 2227-2237.

(36) Gutle, D. D.; Roret, T.; Hecker, A.; Reski, R.; Jacquot, J. P., *Plant Sci.* 2017, 255, 1-11.

(37) Ananikov, V. P.; Gayduk, K. A.; Beletskaya, I. P.; Khrustalev, V. N.; Antipin, M. Y., *Eur. J. Inorg. Chem.* 2009, 2009 (9), 1149-1161.

(38) Fong, J.; Yuan, M.; Jakobsen, T. H.; Mortensen, K. T.; Delos Santos, M. M. S.; Chua, S. L.; Yang, L.; Tan, C. H.; Nielsen, T. E.; Givskov, M., *J. Med. Chem.* 2017, 60 (1), 215-227.

(39) Saito, I.; Fukui, S., *J. Vitaminol.* 1967,13 (2), 115-21.

(40) Müller, A.; Knaack, M.; Olbrich, A., *Magn. Reson. Chem.* 1998, 35 (2), 111-114.

(41) Hayward, L. J.; Rodriguez, J. A.; Kim, J. W.; Tiwari, A.; Goto, J. J.; Cabelli, D. E.; Valentine, J. S.; Brown, R. H., Jr., *J. Biol. Chem.* 2002, 277 (18), 15923-31.

(42) Doucette, P. A.; Whitson, L. J.; Cao, X.; Schirf, V.; Demeler, B.; Valentine, J. S.; Hansen, J. C.; Hart, P. J., *J. Biol. Chem.* 2004, 279 (52), 54558-54566.

(43) Auclair, J. R.; Boggio, K. J.; Petsko, G. A.; Ringe, D.; Agar, J. N., *Proc. Natl. Acad. Sci. U.S.A.* 2010, 107 (50), 21394-9.

(44) Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas; Foresman, J. B.; Ortiz, J. V.; Cioslowski, J.; Fox, D. J., Gaussian 09, Revision B.01. Wallingford CT, 2009.

(45) Zhao, Y.; Truhlar, D. G., *Theor. Chem. Acc.* 2008, 120 (1), 215-241.

(46) Pascual-ahuir, J. L.; Silla, E.; Tuñon, I., *J. Comput. Chem.* 1994, 15 (10), 1127-1138.

(47) Miertts̃, S.; Tomasi, J., *Chem. Phys.* 1982, 65 (2), 239-245.

(48) Miertuš, S.; Scrocco, E.; Tomasi, J., *Chem. Phys.* 1981, 55 (1), 117-129.

(49) Singh, J.; Dobrusin, E. M.; Fry, D. W.; Haske, T.; Whitty, A.; McNamara, D. J., *J. Med. Chem.* 1997, 40 (7), 1130-1135.

(50) Rothwarf, D. M.; Scheraga, H. A., *Proc. Natl. Acad. Sci. U.S.A.* 1992, 89 (17), 7944-7948.

(51) Singh, R.; Whitesides George, M., *Thiol—disulfide interchange*. John Wiley & Sons Ltd: 2010.

(52) Gupta, V.; Carroll, K. S., *Biochim. Biophys. Acta* 2014, 1840 (2), 847-875.

(53) Thapa, B.; Schlegel, H. B., *J. Phys. Chem. A* 2016, 120 (28), 5726-5735.

(54) Singh, R.; Whitesides, G. M., *J. Am. Chem. Soc.* 1990, 112 (3), 1190-1197.

(55) Ullmann, G. M., *J. Phys. Chem. B* 2003, 107 (5), 1263-1271.

The invention claimed is:

1. A polymer derived from a first monomer and a first cross-linker, wherein
the first monomer comprises at least two thiol functional groups;
the first cross-linker comprises a moiety of Formula I:

Formula I wherein
W is S;
Y is S(O);
X together with W and Y forms a substituted or unsubstituted 3-10-membered heterocyclic ring,
the first monomer is selected from the group consisting of poly(ethylene glycol) dithiol, 4arm-PEG2K—SH, 4arm-PEG5K—SH, 4arm-PEG10K—SH, 4arm-PEG20K—SH, 4-arm poly(ethylene oxide) thiol-terminated, 8arm-PEG10K—SH (hexaglyerol core), 8arm-PEG10K—SH (tripentaerythritol core), 8arm-PEG20K—SH (hexaglyerol core), 8arm-PEG20K—SH (tripentaerythritol core), and 8-arm poly(ethylene oxide) thiol-terminated, and
the polymer is a hydrogel.

2. The polymer of claim 1, wherein
X is —$(CR^1R^2)_n$—, wherein n is an integer selected from the group consisting of 1, 2, 3, 4, 5, 6, 7 and 8; and
each $R^1$ and each $R^2$ on each $CR^1R^2$ group is independently selected from the group consisting of H, OH, $NO_2$, CN, $NH_2$, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_2$-$C_{12}$heterocycloalkenyl, optionally substituted $C_6$-$C_{18}$ aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{12}$heteroalkyloxy, optionally substituted $C_3$-$C_{12}$cycloalkyloxy, optionally substituted $C_3$-$C_{12}$cycloalkenyloxy, optionally substituted $C_1$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $CONR^3R^4$, $NR^3COR^4$, $NR^3COOR^4$, $NR^3SO_2R^4$, $NR^3CONR^3R^4$, and $NR^3R^4$; and wherein each $R^3$ and $R^4$ is independently selected from the group consisting of: H, optionally substituted $C_1$-$C_{12}$alkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, and optionally substituted $C_1$-$C_{18}$heteroaryl.

3. The polymer of claim 2, wherein n is an integer selected from the group consisting of 3, 4, 5, and 6.

4. The polymer of claim 3, wherein each $R^1$ and each $R^2$ on each $CR^1R^2$ group is independently selected from the group consisting of H, OH, $NO_2$, CN, $NH_2$, optionally substituted $C_1$-$C_{12}$alkyl, optionally substituted $C_2$-$C_{12}$heteroalkyl, optionally substituted $C_3$-$C_{12}$cycloalkyl, optionally substituted $C_2$-$C_{12}$heterocycloalkyl, optionally substituted $C_1$-$C_{12}$alkyloxy, optionally substituted $C_2$-$C_{12}$heteroalkyloxy, optionally substituted $C_3$-$C_{12}$cycloalkyloxy, and optionally substituted $C_1$-$C_{12}$heterocycloalkyloxy.

5. The polymer of claim 4, wherein each $R^1$ and each $R^2$ on each $CR^1R^2$ group is independently selected from the group consisting of H, OH, $NO_2$, CN, $NH_2$, optionally substituted $C_1$-$C_{12}$alkyl, optionally substituted $C_3$-$C_{12}$cycloalkyl, optionally substituted $C_1$-$C_{12}$alkyloxy, and optionally substituted $C_3$-$C_{12}$cycloalkyloxy.

6. The polymer of claim 1, wherein the first cross-linker comprises a moiety of Formula I selected from the group consisting of

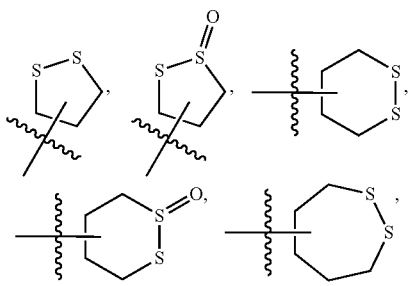

-continued

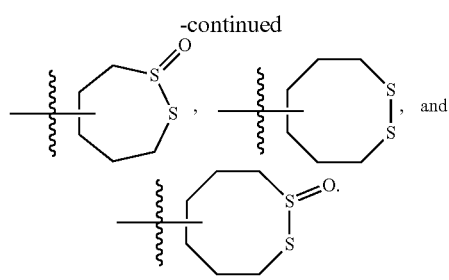

7. A method of preparing the polymer of claim 1, the method comprising providing a plurality of first monomers comprising at least two thiol functional groups, and contacting the plurality of first monomers with a plurality of first cross-linkers comprising a moiety of Formula I, under conditions to enable a reaction to occur between the thiol functional groups and the cross-linker, thereby forming the polymer by covalently cross-linking the monomers via the cross-linkers.

8. The method of claim 7, wherein a plurality of covalent bonds between the S atoms of the first cross-linkers and the thiol functional groups of the first monomers are formed.

9. The method of claim 7, further comprising treating the reaction mixture with an oxidizing agent.

10. The method of claim 7, wherein the reaction occurs in a suitable solvent selected from water, DMSO, DMF, methanol, ethanol, propanol, dichloromethane, and mixtures thereof.

11. The polymer according to claim 6, wherein the first cross-linker comprises a moiety of Formula I represented by

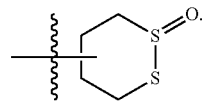

12. The polymer according to claim 11, wherein the first monomer is poly(ethylene glycol) dithiol.

13. The polymer according to claim 11, wherein the first monomer is 4arm-PEG2K—SH, 4arm-PEG5K—SH, 4arm-PEG10K—SH, 4arm-PEG20K—SH, or 4-arm poly(ethylene oxide) thiol-terminated.

14. The polymer according to claim 1, wherein the first monomer is poly(ethylene glycol) dithiol.

15. The polymer according to claim 1, wherein the first monomer is 4arm-PEG2K—SH, 4arm-PEG5K—SH, 4arm-PEG10K—SH, 4arm-PEG20K—SH, or 4-arm poly(ethylene oxide) thiol-terminated.

* * * * *